United States Patent [19]

Boschelli et al.

[11] Patent Number: 5,102,897

[45] Date of Patent: Apr. 7, 1992

[54] 3,5-DITERTIARYBUTYL-4-HYDROXYPHE-NYL, 1,3,4-THIADIAZOLES AND OXADIAZOLES LINKED BY CARBON, OXYGEN, AND SULFUR RESIDUES

[75] Inventors: Diane H. Boschelli, Plymouth; David T. Connor, Ann Arbor; Catherine R. Kostlan, Saline, all of Mich.; James B. Kramer, Sylvania, Ohio; Michael D. Mullican, Ypsilanti; Jagadish C. Sircar, Ann Arbor, both of Mich.

[73] Assignee: Warner-Lambert Company, Morris Plains, N.J.

[21] Appl. No.: 643,212

[22] Filed: Jan. 24, 1991

Related U.S. Application Data

[63] Continuation-in-part of Ser. No. 499,918, Mar. 27, 1990, abandoned.

[51] Int. Cl.[5] .................. C07D 271/113; A61K 31/41
[52] U.S. Cl. ..................................... 514/361; 548/136; 548/141; 548/142; 548/143; 548/144
[58] Field of Search .................. 548/144, 143; 514/361

[56] References Cited

U.S. PATENT DOCUMENTS

| | | | |
|---|---|---|---|
| 3,971,803 | 7/1976 | Rosenberger et al. | 548/144 |
| 4,040,922 | 8/1977 | Wang et al. | 548/144 |
| 4,097,669 | 6/1978 | Reisdorff et al. | 548/144 |
| 4,137,237 | 1/1979 | Durant et al. | 548/144 |
| 4,178,253 | 12/1979 | Lee et al. | 548/144 |
| 4,212,867 | 7/1980 | Boesch | 548/144 |

FOREIGN PATENT DOCUMENTS

| | | |
|---|---|---|
| 0181779 | 5/1986 | European Pat. Off. . |
| 0214732 | 3/1987 | European Pat. Off. . |
| 0269981 | 6/1988 | European Pat. Off. . |
| 0275312 | 7/1988 | European Pat. Off. . |
| 0371438 | 6/1990 | European Pat. Off. . |
| 2533605 | 2/1975 | Fed. Rep. of Germany . |

OTHER PUBLICATIONS

Search Report corresponding EPO Application 91-104 779.
Derwent Abstr. No. 89-151431/21.
Derwent Abstr. No. 88-199351/29.
Derwent Abstr. No. 09605y/06.
Derwent Abstr. No. 70909y/40.

*Primary Examiner*—Robert Gerstl
*Attorney, Agent, or Firm*—Joan Thierstein

[57] ABSTRACT

The novel 3,5-ditertiarybutyl-4-hydroxyphenylthio-1,3,4-thiadiazoles and oxadiazoles and 3,5-ditertiarybutyl-4-hydroxyphenylmethanone-1,3,4-thiadiazoles and oxadiazoles and related compounds of the present invention are antiinflammatory agents having activity as inhibitors of 5-lipoxygenase, cyclooxygenase or both.

23 Claims, No Drawings

3,5-DITERTIARYBUTYL-4-HYDROXYPHENYL, 1,3,4-THIADIAZOLES AND OXADIAZOLES LINKED BY CARBON, OXYGEN, AND SULFUR RESIDUES

This is a continuation-in-part of U.S. application Ser. No. 07/499,918, filed Mar. 27, 1990, now pending.

BACKGROUND OF THE INVENTION 3,5-Ditertiarybutyl-4-hydroxyphenyl is disclosed as a moiety in a variety of compounds.

For example, U.S. application Ser. No. 07/277,171, filed Nov. 29, 1988, now abandoned, and U.S. application Ser. No. 07/426,814, filed Oct. 30, 1989, pending. This moiety linked to thiadiazoles, oxadiazoles, and triazoles. However, the present compounds differ from this disclosure by the addition of either a carbonyl, an oxygen, carbon containing oxime, a sulfur, an oxygenated sulfur, or alkyl carbonyl moieties between the 3,5-di-tertiarybutyl-4-hydroxyphenyl and a 1,3,4-thiadiazole or oxadiazole ring.

Other references disclose compounds combining a 3,5-ditertiarybutyl-4-hydroxyphenyl with various other rings such as pyrazoles, isoxazoles or imidazoles. See copending Application U.S. application Ser. No. 06/861,179, filed May 9, 1986, now abandoned; U.S. application Ser. No. 06/910,692, filed Sept. 26, 1986, now abandoned; U.S. application Ser. No. 07/032,730, filed Apr. 6, 1987, now abandoned; and U.S. application Ser. No. 07/395,165, filed Aug. 16, 1989, now pending. However, such references differ from the present invention in both the heteroaryl ring moiety and the substituent between the heteroaryl ring and the 3,5-ditertiarybutyl-4-hydroxylphenyl moiety. The present invention is limited to rings having three heteroatoms together with a CO, S, S(O)$_n$, O, O(CH$_2$)$_m$,

S(O)$_n$(CH$_2$)$_m$, (CH$_2$)$_m$, or CO(CH$_2$)$_m$ between the rings.

SUMMARY IN THE INVENTION

The present invention is a novel compound of the Formula I

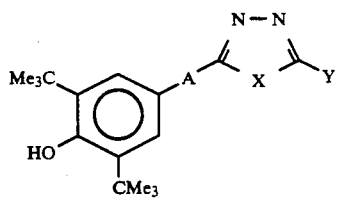

and pharmaceutically acceptable base or acid addition salt thereof; in which A is CO, C=NOH, S(O)$_n$(CH$_2$)$_m$, S(O)$_n$, (CH$_2$)$_m$, CO(CH$_2$)$_m$, O, or O(CH$_2$)$_m$; wherein X is O, or S;

Y is H, OH, SH, NH$_2$, NHCN,

SCH$_3$, SOCH$_3$ or SO$_2$CH$_3$; R is hydrogen or lower alkyl; and n is an integer of zero, one or two; and m is an integer of one or two with the proviso that when A is (CH$_2$)$_2$ and Y is OH then X cannot be O.

The present invention is also a pharmaceutical composition for treating a disease or condition, such as rheumatoid arthritis, osteoarthritis, other inflammatory conditions, psoriasis, allergic diseases, inflammatory bowl disease, GI ulcers, cardiovascular conditions including ischemic heart disease, and atherosclerosis and ischemia-induced cell damage particularly brain damage caused by stroke; preferably antiinflammatory disease or condition, comprising an antiinflammatory, antipsoriatic, antiallergy, antiulcer, or antiischemic, antiatherosclerotic, or cytoprotective amount of the compound of the Formula I or as a pharmaceutically acceptable salt thereof as defined above and a pharmaceutically acceptable carrier.

The present invention is also a method of treating a disease or condition as noted above in a mammal, particularly a human, suffering therefrom which comprises administering a compound of the Formula I or salt thereof as defined above in unit dosage form.

The invention also provides for use of any such compound of Formula I or salt thereof in the manufacture of a medical therapeutic agent.

The pharmaceutical composition or method of treating which is the present invention is meant to include what is understood to be prophylactic to one of a foregoing named disease or condition.

The compounds of the Formula I have activity as inhibitors of 5-lipoxygenase, cyclooxygenase or both to provide the use for the pharmaceutical composition and methods of the present invention.

A preferred compound of the Formula I is
5-[[3,5-Bis(1,1-dimethylethyl)-4-hydroxyphenyl]thio]-1,3,4-oxadiazole-2(3H)-thione,
5-[[3,5-Bis(1,1-dimethylethyl)-4-hydroxyphenyl]thio]-1,3,4-oxadiazol-2(3H)-one,
2,6-Bis(1,1-dimethylethyl)-4-[(1,3,4-thiadiazol-2-yl)thio]phenol,
2,6-Bis(1,1-dimethylethyl)-4-[2-(1,3,4-oxadiazol-2-yl)ethyl]phenol,
5-[[3,5-Bis(1,1-dimethylethyl)-4-hydroxyphenyl]thio]-1,3,4-thiadiazole-2(3H)-thione,
5-[[3,5-Bis(1,1-dimethylethyl)-4-hydroxy-phenylthio]ethyl]-1,3,4-oxadiazol-2(3H)-one,
2,6-Bis(1,1-dimethylethyl)-4-[[2-(1,3,4-oxadiazol-2-yl)ethyl]thio]phenol, and
(5-Amino-1,3,4-thiadiazol-2-yl)[3,5-bis(1,1-dimethylethyl)-4-hydroxyphenyl]methanone.

More preferred are
5-[[3,5-Bis(1,1-dimethylethyl)-4-hydroxyphenyl]thio]-1,3,4-thiadiazole-2(3H)-thione,
5-[2-[[3,5-Bis(1,1-dimethylethyl)-4-hydroxyphenyl]thio]ethyl-1,3,4-oxadiazol-2(3H)-one,
2,6-Bis(1,1-dimethylethyl)-4-[[2-(1,3,4-oxadiazol-2-yl)ethyl]thio]phenol, and
(5-Amino-1,3,4-thiadiazol-2-yl)3,5-bis(1,1-dimethylethyl)-4-hydroxyphenyl]methanone.

The most preferred is
5-[[3,5-Bis(1,1-dimethylethyl)-4-hydroxyphenyl]-thio]-1,3,4-oxadiazole-2(3H)-thione.

DETAILED DESCRIPTION OF THE INVENTION

In the present invention "lower alkyl" is alkyl of from one to six carbons, inclusive, and means methyl, ethyl, propyl, butyl, pentyl or hexyl and isomers thereof.

"Halogen" is chloro, iodo, bromo or fluoro.

Me is methyl.

The compounds of the invention may contain geometric isomers. Thus, the invention includes the individual isomers and mixtures thereof. The individual isomers may be prepared or isolated by methods known in the art.

A tautameric form of selected compounds of Formula I would be recognized by an ordinarily skilled artisan to be within the present invention.

The compounds of Formula I are useful both in the free base and where possible the free acid form or in the form of base salts thereof, as well as, in the form of acid addition salts. All forms are within the scope of the invention. In practice, use of the salt form amounts to use of the free acid or free base form. Appropriate pharmaceutically acceptable salts within the scope of the invention are those derived from mineral acids such as hydrochloric acid and sulfuric acid; and organic acids such as methanesulfonic acid, benzenesulfonic acid, maleic acid, p-toluenesulfonic acid, and the like, giving the hydrochloride, sulfamate, methanesulfonate, benzenesulfonate, p-toluenesulfonate, and the like, respectively, or those derived from bases such as suitable organic and inorganic bases. Examples of suitable inorganic bases for the formation of salts of compounds of this invention include the hydroxides, carbonates, and bicarbonates of ammonia, sodium, lithium, potassium, calcium, magnesium, aluminum, zinc, and the like.

Salts may also be formed with suitable organic bases. Bases suitable for the formation of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines, such as methylamine, dimethylamine, and triethylamine; choline; mono-, di-, or trihydroxyalkylamines such as mono-, di-, and triethanolamine; amino acids such as arginine, and lysine; choline; guanidine; N-methylglucosamine; N-methylpiperazine; morpholine; ethylenediamine; N-benzylphenethylamine; tris(hydroxymethyl) aminomethane; and the like. (See for example, "Pharmaceutical Salts," *J. Pharm. Sci.*, 66(1), 1-19 (1977).)

The acid addition salts of said compounds are prepared either by dissolving the free base of compound I in aqueous or aqueous alcohol solution or other suitable solvents containing the appropriate acid or base and isolating the salt by evaporating the solution, or by reacting the free base of compound I with an acid as well as reacting compound I having an acid group thereon with a base such that the reactions are in an organic solvent, in which case the salt separates directly or can be obtained by concentration of the solution.

The base salts of compounds of Formula I described above are prepared by reacting the appropriate base with a stoichiometric equivalent of the acid compounds of Formula I to obtain pharmacologically acceptable base salts thereof.

The present invention also includes the solvates or hydrates of compounds of this invention, when possible, and are prepared or isolated by methods known in the art.

The usefulness of the compounds of the present invention as inhibitors of the 5-lipoxygenase enzyme, cyclooxygenase, or in treating related diseases or conditions may be demonstrated by their effectiveness in various standard test procedures. A description of each procedure follows.

ARBL/ARBC Whole Cell 5-Lipoxygenase and Cyclooxygenase Assays

Materials

The rat basophilic leukemia cell line (RBL-1) was obtained from the American Type Culture Collection (Rockville, MD).

Radioimmunoassay (RIA) kits of $LTB_4$ and $PGF_{2\alpha}$ were obtained from Amersham (Arlington Heights, Ill.) and Seragen (Boston, Mass.), respectively.

All tissue culture media were obtained from GIBCO (Grand Island, N.Y.).

Method

RBL-1 cells are grown in suspension culture in Eagle's minimum essential medium supplemented with 12% fetal bovine serum at 37° C. in an incubator supplied with air-5% carbon dioxide. Cells are harvested by centrifugation. They are washed with cold phosphate buffered saline pH 7.4 (PBS; NaCl, 7.1 g; $Na_2HPO_4$, 1.15 g; $KH_2PO_4$, 0.2 g; and KCl, 0.2 g/L). Cells are finally suspended in PBS containing 1.0 mM calcium at a density of $2 \times 10^6$ cells/mL. Cells are incubated with and without test agent (in DMSO) (1% DMSO is without effect on arachidonic acid metabolism) for ten minutes at room temperature. Calcium ionophore A23187 (5 $\mu M$) is added and cells are incubated for 7 minutes at 37° C. The reaction is stopped by chilling the tubes on ice for 10 minutes. Cells are separated by centrifugation and the supernatant is stored at $-20°$ C. Aliquots (100 $\mu L$) are analyzed for $LTB_4$ and $PGF_{2\alpha}$ using radioimmunoassay kits as provided by the supplier.

Table 1 contains biochemical data obtained from this whole cell assay as $IC_{50}s$ which are calculated as the amount of test compound causing 50% inhibition or percent of inhibition at the named micromoles ($\mu M$) of $LTB_4$ or $PGF_{2\alpha}$ formation.

Carrageenan-Induced Rat Foot Paw Edema-2 (CFE-2) Assay: Protocol

Carrageenan solution (1% w/v) is prepared by dissolving 100 mg carrageenan (Marine Colloidal Div., Springfield, N.J.) in 10 mL of sterile saline (0.9) solution (Travenol). The solution is vortexed for 30 to 45 minutes. Animals are dosed with compound 1 hour before carrageenan challenge. Foot paw edema is induced by injecting 0.10 mL of the 1% carrageenan subcutaneously into the plantar portion of the right hind paw of each rat under light anesthesia. Initial foot paw volume is measured immediately following carrageenan challenge using mercury plethysmography (Buxco Electronics). Edema is measured 5 hours after carrageenan. The difference between the 5-hour and the initial paw volume is expressed as delta edema. The delta edema for each test group of animals is used to calculate the percent inhibition of edema achieved by the compound at the test dose compared with the vehicle control group. The data in Table 1 (the dose at which swelling is inhibited by the noted) is calculated by probit analysis for the dose at which percent inhibition occurs.

TABLE 1

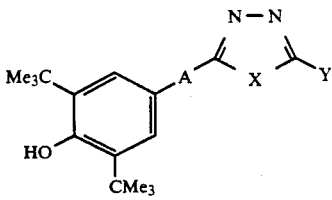

| Example | A | X | Y | ARBL | ARBC | CFE |
|---|---|---|---|---|---|---|
| 6 | S | O | OH | 91 @ 16[b] | 46 @ 16[d] | |
| 7 | S | O | SH | 2[a] | 1.5[c] | 8.6[f] |
| 8 | S | S | OH | 90 @ 16[b] | N[e] | |
| 9 | S | S | SH | 1.1[a] | 3.6[c] | |
| 10 | S | S | H | 59 @ 10[b] | 54 @ 10[d] | |
| 13 | S(CH$_2$)$_2$ | O | OH | 0.6[a] | 75 @ 10[d] | |
| 14 | S(CH$_2$)$_2$ | O | SH | 4.2[a] | N[c] | |
| 15 | S(CH$_2$)$_2$ | O | H | 100 @ 10[b] | 55 @ 10[d] | |
| 16 | S(CH$_2$)$_2$ | O | NH$_2$ | 100 @ 10[b] | N[e] | |
| 23 | (CH$_2$)$_2$ | O | OH | 60 @ 10[b] | N[e] | |
| 25 | (CH$_2$)$_2$ | O | H | 100 @ 10[b] | 52 @ 10[d] | |
| 26 | (CH$_2$)$_2$ | O | NH$_2$ | 40 @ 10[b] | N[e] | |
| 29 | CO | S | NH$_2$ | 1.1[a] | 5.2[c] | |
| 30 | CO | S | SMe | 100 @ 10 | 100 @ 10 | |
| 31 | CO | S | SH | 100 @ 10 | 92 @ 10 | |

[a]IC$_{50}$ for LTB$_4$ inhibition
[b]Percent inhibition of LTB$_4$ @ μM noted
[c]IC$_{50}$ for PGF$_{2\alpha}$ inhibition
[d]Percent inhibition of PGF$_{2\alpha}$ @ 10 μM
[e]N is not active at the dose tested
[f]ID$_{40}$ (mg/kg) for inhibition of swelling Accordingly, the present invention also includes a pharmaceutical composition for treating one of the above diseases or conditions comprising an antidisease effective amount or an amount effective for the inhibition of 5-lipoxygenase, cyclooxygenase or both of a compound of the Formula I or salt thereof, as defined above together with a pharmaceutically acceptable carrier.

The present invention further includes a method for treating one of the above named diseases or conditions in mammals, including man, suffering therefrom comprising administering to such mammals either orally or parenterally, preferably oral, a corresponding pharmaceutical composition containing a compound of the Formula I or salt thereof.

A physician or veterinarian of ordinary skill readily determines a subject who is exhibiting symptoms of any one or more of the diseases described above. Regardless of the route of administration selected, the compounds of the present invention of the Formula I as described in pharmaceutical compositions above are formulated into pharmaceutically acceptable dosage forms by conventional methods known to the pharmaceutical art.

The compounds can be administered in such oral unit dosage forms as tablets, capsules, pills, powders, or granules. They also may be administered rectally or vaginally in such forms as suppositories or bougies; they may also be introduced parenterally (e.g., subcutaneously, intravenously, or intramuscularly), using forms known to the pharmaceutical art. They are also introduced directly to an affected area (e.g., in the form of eye drops or by inhalation). For the treatment of asthma or allergies, particularly dermatological disorders; such as erythema, psoriasis and acne, the compounds may also be administered topically in the form of ointments, gels, or the like However, in general, the preferred route of administration is orally.

An effective but nontoxic quantity of the compound is employed in treatment. The ordinarily skilled physician or veterinarian will readily determine and prescribe the effective amount of the compound to prevent or arrest the progress of the condition for which treatment is administered. In so proceeding, the physician or veterinarian could employ relatively low dosages at first, subsequently increasing the dose until a maximum response is obtained.

In determining when a lipoxygenase, cyclooxygenase, or dual lipoxygenase/cyclooxygenase inhibitor is indicated, of course inter alia, the particular condition in question and its severity, as well as the age, sex, weight, and the like of the subject to be treated, must be taken into consideration and this determination is within the skill of the attendant physician.

For medical use, the amount required of a compound of Formula I or pharmacologically acceptable salt thereof to achieve a therapeutic effect will, of course, vary both with the particular compound, the route of administration, the mammal under treatment, and the particular disorder or disease concerned. A suitable dose of a compound of Formula I or pharmacologically acceptable salt thereof for a mammal suffering from, or likely to suffer from any condition as described hereinbefore is 0.1 μg–500 mg of the compound per kilogram body weight. In the case of systemic administration, the dose may be in the range of 0.5 to 500 mg of the compound per kilogram body weight, the most preferred dosage being 0.5 to 50 mg/kg of mammal body weight administered two or three times daily. In the case of topical administration, e.g., to the skin or eye, a suitable dose may be in the range 0.1 ng–100 μg of the compound per kilogram, typically about 0.1 μg/kg.

In the case of oral dosing for the treatment or prophylaxis of arthritis or inflammation in general, due to any course, a suitable dose of a compound of Formula I or physiologically acceptable salt thereof, may be specified in the preceding paragraph, but most preferably is from 1 mg to 10 mg of the compound per kilogram, the most preferred dosage being from 1 mg to 5 mg/kg of mammal body weight, for example for 1 to 2 mg/kg It is understood that the ordinarily skilled physician or veterinarian will readily determine and prescribe the effective amount of the compound to prevent or arrest the progress of the condition for which treatment is administered. In so proceeding, the physician or veterinarian could employ relatively low doses at first, subsequently increasing the dose until a maximum response is obtained.

While it is possible for an active ingredient to be administered alone, it is preferable to present it as a pharmaceutical formulation comprising a compound of Formula I or a pharmacologically acceptable acid addition or base salt thereof and a pharmacologically acceptable carrier therefor. Such formulations constitute a further feature of the present invention.

In addition to the compounds of Formula I, the pharmaceutical compositions can also contain other active ingredients, such as cyclooxygenase inhibitors, nonsteroidal antiinflammatory drugs (NSAIDs), peripheral analgesic agents such as zomepirac, diflunisal, and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID, the weight ratio of the compound of the formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Combinations of a compound of the Formula I and other active ingredients will generally be in the aforementioned ratios.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams or a pharmaceutically acceptable salt thereof.

The propionic acid derivatives which may be used comprise: ibuprofen, ibuprufen aluminum, indoprofen, ketoprofen, naproxen, benoxaprofen, flurbiprofen, fenoprofen, fenbufen, pirprofen, carprofen, oxaprozin, pranoprofen, miroprofen, tioxaprofen, suprofen, alminoprofen, tiaprofen, fluprofen, and bucloxic acid. Structurally related propionic acid derivatives having similar analgesic and antiinflammatory properties are also intended to be included in this group.

Thus, "propionic acid derivatives" as defined herein are nonnarcotic analgesics/nonsteroidal anti-inflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$NA$^+$ or —CH$_2$CH$_2$COO$^-$Na$^+$), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structurally related acetic acid derivatives having similar analgesic and antiinflammatory properties are also intended to be encompassed by this group.

Thus, "acetic acid derivatives" as defined herein are nonnarcotic analgesics/nonsteroidal antiinflammatory drugs having a free —CH$_2$COOH group (which optionally can be in the form of a pharmaceutically acceptable salt group, e.g. —CH$_2$COO$^-$Na$^+$), typically attached directly to a ring system, preferably to an aromatic or heteroaromatic ring system.

The fenamic acid derivatives which may be used comprise: mefanamic acid, meclofenamic acid, flufenamic acid, niflumic acid, and tolfenamic acid. Structurally related fenamic acid derivatives having similar analgesic and antiinflammatory properties are also intended to be encompassed by this group.

Thus, "fenamic acid derivatives" as defined herein are nonnarcotic analgesics/nonsteroidal antiinflammatory drugs which contain the basic structure:

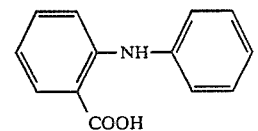

which can bear a variety of substituents and in which the free —COOH group can be in the form of a pharmaceutically acceptable salt group, e.g., —COO$^-$Na$^+$.

The biphenylcarboxylic acid derivatives which can be used comprise: diflunisal and flufenisal. Structurally related biphenylcarboxylic acid derivatives having similar analgesic and antiinflammatory properties are also intended to be encompassed by this group.

Thus, "biphenylcarboxylic acid derivatives" as defined herein are nonnarcotic analgesics/nonsteroidal antiinflammatory drugs which contain the basic structure:

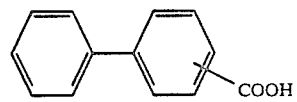

which can bear a variety of substituents and in which the free —COOH group can be in the form of a pharmaceutically acceptable salt group, e.g., —COO$^-$Na$^+$.

The oxicams which can be used in the present invention comprise: piroxicam, sudoxicam, isoxicam, and 4-hydroxyl-1,2-benzothiazine 1,1-dioxide 4-(N-phenyl)-carboxamide. Structurally related oxicams having similar analgesic and antiinflammatory properties are also intended to be encompassed by this group.

Thus, "oxicams" as defined herein are nonnarcotic analgesics/nonsteroidal antiinflammatory drugs which have the general formula:

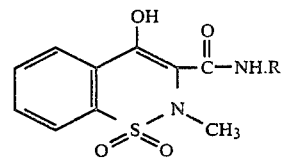

wherein R is an aryl or heteroaryl ring system.

The following NSAIDs may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin, clonixinate, meclofenamate sodium, meseclazone, microprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

Finally, NSAIDs which may also be used include the salicylates, specifically aspirin, and the phenylbutazones, and pharmaceutically acceptable salts thereof.

Pharmaceutical compositions comprising the formula I compounds may also contain as the second active ingredient, antihistaminic agents such as benadryl, dramamine, histadyl, phenergan, and the like. Alternatively, they may include prostaglandin antagonists such as those disclosed in European Patent Application 11,067 or thromboxane antagonists such as those disclosed in U.S. Pat. No. 4,237,160. They may also α-fluoromethylhistidine, described in U.S. Pat. No. 4,325,961. The compounds of the formula I may also be advantageously combined with an $H_1$ or $H_2$-receptor antagonist, such as for instance cimetidine, ranitidine, terfenadine, famotidine, temelastine, acrivastine, loratadine, cetrizine, tazifylline, azelastine, aminothiadiazoles disclosed in EP 81102976.8 and like compounds, such as those disclosed in U.S. Pat. Nos. 4,283,408; 4,362,736; 4,394,508, and European Patent Application No. 40,696. The pharmaceutical compositions may also contain a $K^+/H^+$ ATPase inhibitor such as omeprazole, disclosed in U.S. Pat. No. 4,255,431, and the like. Each of the references referred to in this paragraph is hereby incorporated herein by reference.

The compounds of the Formula I are prepared generally by the following processes and constitute a further aspect of the present invention.

Generally, the compounds of Formula I are prepared by one of the following methods shown hereinafter in Schemes I, II, III, IV, and V.

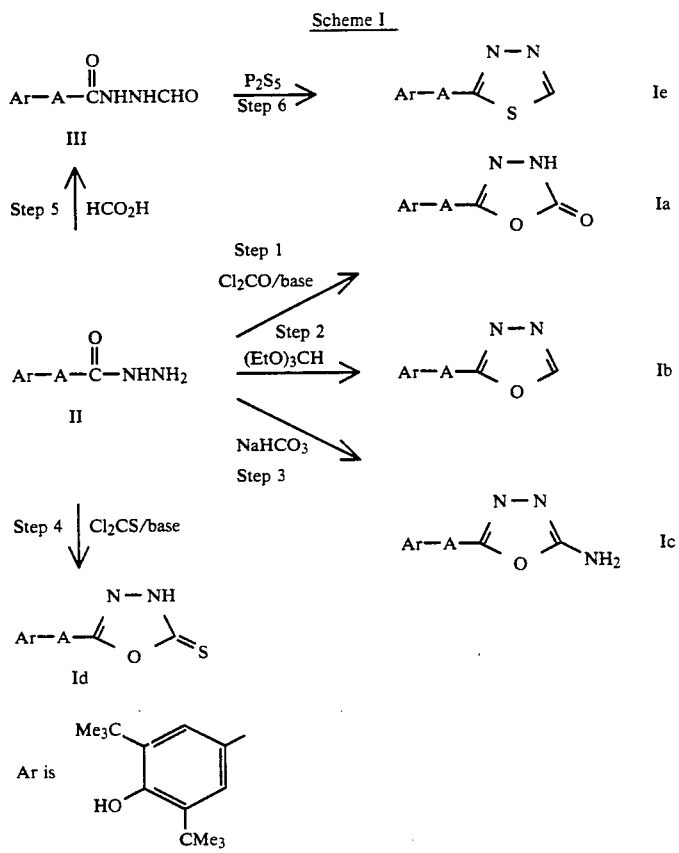

A is S, S(CH$_2$)$_m$, (CH$_2$)$_m$, CO(CH$_2$)$_m$

Description of Scheme I

In Step 1 of Scheme I, a hydrazide of Formula II is treated with phosgene, or a phosgene equivalent such as 1,1'-carbonyldiimidazole, in the presence of 0-3 equivalents of an organic base such as triethylamine, pyridine, or preferably diisopropyethyl amine, to give an oxadiazolone of Formula Ia. Suitable solvents for this reaction include tetrahydrofuran and methylene chloride.

In Step 2, a hydrazide of Formula II is treated with an orthoformic ester, preferably triethyl orthoformate, along with a catalytic amount of an organic acid such as p-toluenesulfonic acid or a mineral acid such as HCl, either neat or in an alcoholic solvent, preferably ethanol, to provide an oxadiazole of Formula Ib.

In Step 3, a hydrazide of Formula II is dissolved in a suitable solvent such as tetrahydrofuran or dioxane and treated with cyanogen bromide followed by an aqueous solution of an inorganic base, such as sodium bicarbonate, to provide an amino-oxadiazole of Formula Ic.

In Step 4, a hydrazide of Formula II is treated with 1,1'-thiocarbonyldiimidazole or preferably thiophosgene, in the presence of 0-3 equivalents of an organic base such as diisopropylethylamine, in a solvent such as tetrahydrofuran to give an oxadiazolethione of Structure Id. This transformation can also be achieved by refluxing a solution of the hydrazide of Formula II with carbon disulfide in absolute ethanol or methanol in the presence of an inorganic base such as potassium hydroxide.

In Step 5, a hydrazide of Formula II is formylated in neat formic acid. Subsequent treatment of Intermediate III with phosphorous pentasulfide or other thionating agent, such as Lawesson's Reagent, in a solvent such as dioxane or tetrahydrofuran yields a thiadiazole of Formula Ie.

Scheme II

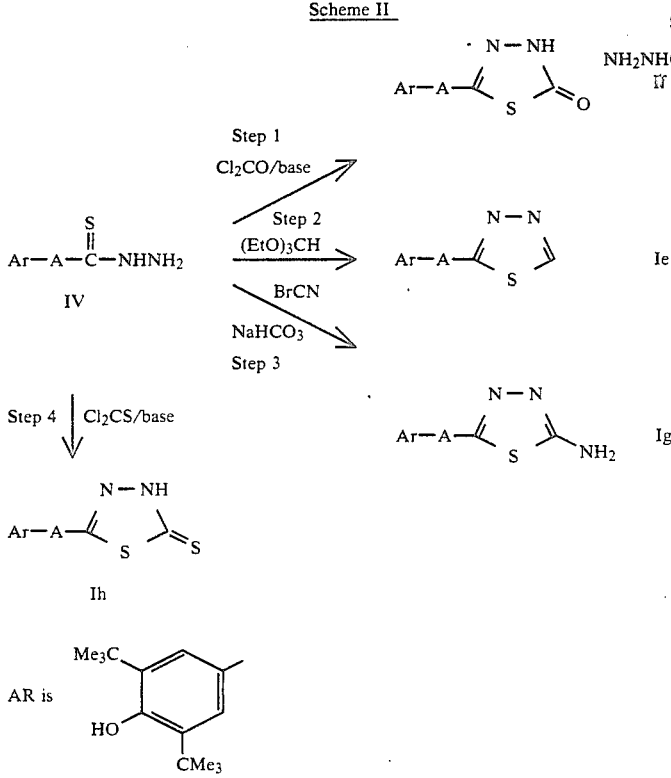

AR is

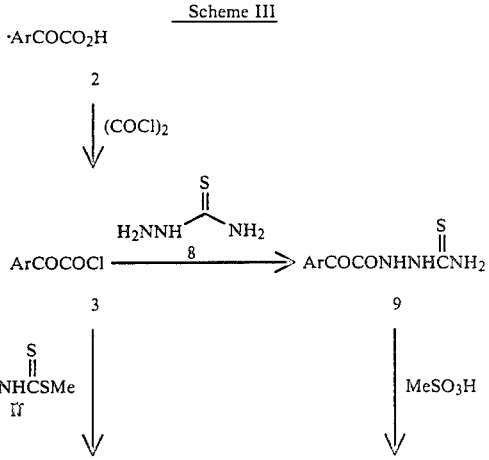

A is S, S(CH$_2$)$_m$, (CH$_2$)$_m$, CO(CH$_2$)$_m$

Description of Scheme II

In Scheme II, thiohydrazides of Formula IV are subjected to the same conditions used to convert hydrazides of Formula II to oxadiazoles of Formula Ia, Ib, Ic, and Id. The result is the preparation of thiadiazoles of Formula If, Ie, Ig, and Ih analogous to the aforementioned oxadiazoles. It should be noted that thiadiazoles of Formula Ie can also be prepared by the route shown in Scheme I.

Scheme III

ArCOCO$_2$CH$_3$

1

↓ NaOH

-continued
Scheme III

ArCOCO$_2$H

2

↓ (COCl)$_2$

ArCOCOCl  →[H$_2$NNH-C(S)-NH$_2$, 8]  ArCOCONHNHC(S)NH$_2$ 3     9

↓ NH$_2$NHC(S)SMe, 11    ↓ MeSO$_3$H

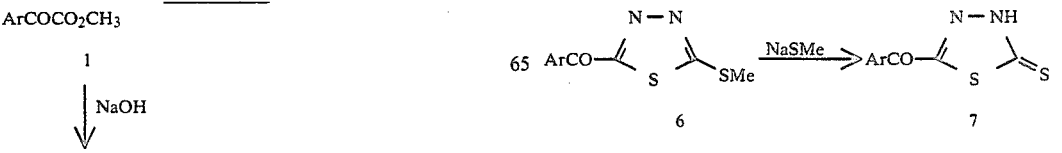

Ar is 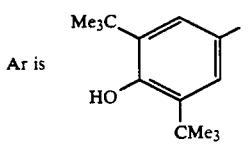

pound 7 can be prepared from 6 using sodium thiomethoxide in DMF at 0° C. to 100° C. for 1 hour to 7 days.

Compound 3 can also be treated with thiosemicarbazide in pyridine or ether solvents to give 9. Treatment of 9 with acids such as hydrochloric acid, methanesulfonic acid, or toluenesulfonic acids gives compound 10.

Scheme IV

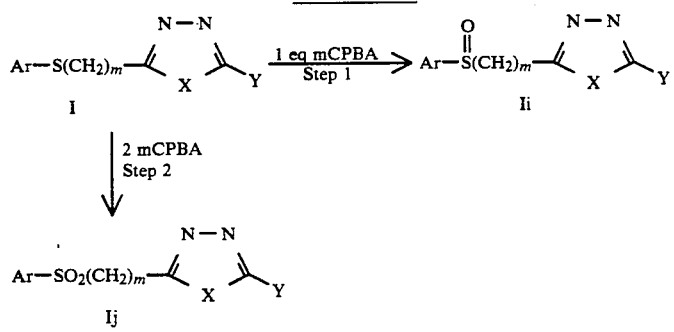

Scheme V

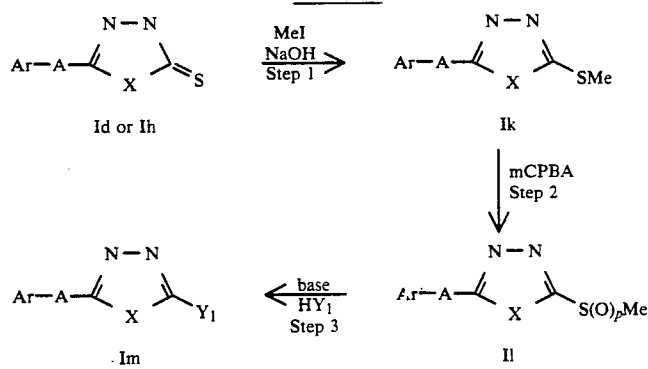

Ar, A, and X are as defined in Structure I $Y_1$ is NHCN, NH—C(=NH)—NHR

Description of Scheme III

In Scheme III, saponification of ester 1 to compound 2 using an aqueous alkali base including KOH, NaOH, are LiOH in alcoholic and/or ethers solvents (such as tetrahydrofuran, diethyl ether, dioxane, t-butylmethyl ether, or diisopropyl ether) at temperatures from 0° C. to 100° C. for 1 hour to 7 days. The acid chloride 3 can be prepared from 2 using oxalyl chloride and a catalytic amount of N,N-dimethylformamide (DMF) in ether or halogenated solvents (such as dichloromethane, chloroform, dichloroethane, or dichlorobenzene). Thionylchloride may also be used for this conversion. Reaction temperatures can range from 0 to 100° C. for times of 1 hour to 7 days. Compound 3 can be treated with hydrazinecarbodithionic acid, methylester (4; Audrieth, L. F.; Scott, E. S.; Kippur, P. S., *J. Org. Chem.* 1954, 19, 733) in ether solvents at temperatures of 0° C. to 100° C. for 1 hour to 7 days to give compound 5. Treatment of 5 with acids such as hydrochloric acid, methanesulfonic acid, or p-toluenesulfonic acid in aromatic or ether solvents at 0° C. to 100° C. will give compound 6. Com-

Description of Scheme IV

In Step 1 of Scheme IV, those compounds of Formula I where Y does not contain sulfur are treated with an equivalent amount of m-chloroperbenzoic acid in methylene chloride to provide compounds of Formula Ii. Other suitable oxidizing agents are $KMnO_4$, $NaIO_4$, and hydrogen peroxide. In Step 2, the use of two or more equivalents of oxidizing agent, again preferably m-chloroperbenzoic acid, converts compounds of Formula I to compounds of Formula Ij.

Description of Scheme V

In Step 1 of Scheme V, compounds of Formula Id or Ih are treated with iodomethane in the presence of a base such as potassium hydride, potassium t-butoxide, or preferably sodium hydroxide in a solvent such as dimethylformamide or preferably methanol to provide compounds of Formula Ik. In Step 2, those compounds of Formula Ik where A does not contain sulfur are oxidized with either 1 or 2 or more equivalents of an oxidizing agent, preferably m-chloroperbenzoic acid to give a compound of Formula II where p=1 or 2*. In Step 3, compounds of Formula II are treated with cyanamide or guanidine-HCl in the presence of an inorganic base preferably potassium t-butoxide in a solvent such as t-butanol to provide compounds of Formula Im. Compounds of Formula Im where Y'=NHCN can also be prepared by treatment of a compound of Formula II with cyanamide and an organic base, preferably triethylamine, in a solvent such as dimethylformamide.

* If A is S, sodium perborate is used for the oxidation.

One of skill in the art would recognize variations in the sequence and would recognize variations in the appropriate reaction conditions from the analogous reactions shown or otherwise known which may be appropriately used in the processes above to make the compounds of the Formula I herein.

In the process described herein for the preparation of compounds of this invention the requirements for protective groups are generally well recognized by one skilled in the art of organic chemistry, and accordingly the use of appropriate protecting groups is necessarily implied by the processes of the charts herein, although such groups may not be expressly illustrated.

Introduction and removal of such suitable oxygen protecting groups are well-known in the art of organic chemistry; see for example "Protective Groups in Organic Chemistry," J. F. W. McOmie, ed., (New York, 1973), pages 43ff, 95ff, J. F. W. McOmie, *Advances in Organic Chemistry*, Vol. 3, 159-190 (1963); J. F. W. McOmie, *Chem & Ind.*, 603 (1979), and T. W. Greene, "Protective Groups in Organic Synthesis", Wiley (New York) 1981, Chapters 2, 3, and 7.

Examples of suitable oxygen protecting groups are benzyl, trialkylsilyl, ethoxyethyl, methoxyethoxymethyl, methoxymethyl, trialkylsilylethyl, and the like.

The products of the reactions described herein are isolated by conventional means such as extraction, distillation, chromatography, and the like.

Starting materials not described herein are available commercially, are known, or can be prepared by methods known in the art.

The salts of the compounds of Formula I described above are prepared by reacting the appropriate base or acid with a stoichiometric equivalent of the compounds of Formula I.

The invention is further elaborated by the representative examples as follows. Such examples are not meant to be limiting.

EXAMPLE 1

3,5-Bis(1,1-dimethylethyl)-4-hydroxyphenyl thiocyanate 3,5-Bis(1,1-dimethylethyl)-4-hydroxyphenyl thiocyanate is prepared according to the method of European Patent Number 0 293 900, assigned to G.bD. Searle & Co.

EXAMPLE 2

2,6-Bis(1,1-dimethylethyl)-4-mercaptophenol 2,6-Bis(1,1-dimethylethyl)-4-mercaptophenol is prepared according to the method of European Patent Number 0 293 900, assigned to G. D. Searle & Co.

EXAMPLE 3

S,S-Bis[3,5-bis(1,1-dimethylethyl)-4-hydroxyphenyl]-carbonodithioate

N,N-Diisopropylethylamine (21.6 mL, 125.8 mmol) is added to a −48° C. solution of 2,6-bis(1,1-dimethylethyl)-4-mercaptophenol (20.0 g, 84.0 mmol) in toluene (400 mL) followed by dropwise addition of a 12.5% solution of phosgene in toluene (33.2 g, 42.0 mmol). The reaction mixture is stirred for 1.5 hours then poured into a separatory funnel containing ethyl acetate and water. The aqueous phase is acidified to pH 3 with 1N hydrochloric acid. The organic phase is washed twice with water, then with a saturated solution of sodium bicarbonate followed by brine. Drying the organic phase over magnesium sulfate and evaporation of the solvents gives a heavy oil which is crystallized from isopropyl ether/hexane to afford 9.6 g (46%) of S,S-bis[3,5-bis(1,1-dimethylethyl)-4-hydroxyphenyl]carbonodithionate, mp 176.0–178.0° C.

Analysis for $C_{29}H_{42}S_2O_3$:
Calcd: C, 69.28; H, 8.42.
Found: C, 69.17, H, 8.50.

EXAMPLE 4

S-[3,5-Bis(1,1-dimethylethyl)-4-hydroxyphenyl]hydrazinecarbothioate

A solution of S,S-bis[3,5-bis(1,1-dimethylethyl)-4-hydroxyphenyl] carbonodithioate (5.0 g, 9.9 mmol) in dichloromethane (50 mL) is added dropwise to a 0° C. solution of hydrazine monohydrate (1.1 g, 22.0 mmol) in dichloromethane (60 mL). The ice bath is removed and the reaction is stirred vigorously for 48 hours. The reaction mixture is diluted with ethyl acetate and washed four times with water and once with brine. The organic phase is dried over magnesium sulfate and the solvents are evaporated in vacuo. The residue is chromatographed on a 100 g silica column with ethyl acetate/hexane (1/9 then 1/1). The hydrazide is crystallized from isopropyl ether to give 2.72 g (92%) of S-[3,5-bis(1,1-dimethylethyl)-4-hydroxyphenyl] hydrazinecarbothioate, mp 130.0–131.0° C.

Analysis for $C_{15}H_{24}N_2O_2S$:
Calcd: C, 60.78; H, 8.16; N, 9.45; S, 10.82.
Found: C, 61.05, H, 8.29; N, 9.49; S, 10.79.

EXAMPLE 5

3,5-Bis(1,1-dimethylethyl)-4-hydroxyphenyl hydrazinecarbodithioate

Thiophosgene (1.6 mL, 21.0 mmol) is added dropwise to a −78° C. solution of 2,6-bis(1,1-dimethylethyl)-4-mercaptophenol (5.0 g, 21.0 mmol) and N,N-diisopropylethylamine (5.4 mL, 31.4 mmol) in toluene/dichloromethane (100 mL/20 mL). The reaction mixture is stirred for 1.5 hours then poured into a separatory funnel containing ethyl acetate and water. The aqueous phase is acidified to pH 3 with 1N hydrochloric acid. The organic phase is washed twice with water, then with a saturated solution of sodium bicarbonate followed by brine. Drying the organic phase over magnesium sulfate and evaporation of the solvents gives a crude product which is dissolved in dichloromethane (200 mL) and cooled to 0° C. Hydrazine monohydrate (1.5 mL, 31.0 mmol) is added in three portions at 30 minute intervals, and the solution is stirred for 1 hour. The reaction is poured into ethyl acetate and washed four times with an aqueous solution of sodium chloride and once with a saturated solution of sodium chloride. Drying the organic phase over magnesium sulfate and evaporation gives an amorphous solid which is crystallized from 50 mL of ethyl acetate/hexane (5/95) affording 3.5 g (53% from 2,6-bis(1,1-dimethylethyl)-4-mercaptophenol) of 3,5-bis(1,1-dimethylethyl)-4-hydroxyphenyl hydrazinecarbodithioate, mp 145.5°–146.0° C.

Analysis for $C_{15}H_{24}N_2OS_2$:
Calcd: C, 57.65; H, 7.74; N, 8.96.
Found: C, 57.30; H, 7.74; N, 8.68.

EXAMPLE 6

5-[[3,5-Bis(1,1-dimethylethyl)-4-hydroxyphenyl]thio]-1,3,4-oxadiazol-2(3H)-one

A 12.5% solution of phosgene in toluene (13.0 mL, 13.5 mmol) is added dropwise to a −78° C. solution of S-[3,5-bis(1,1-dimethylethyl)-4-hydroxyphenyl] hydrazinecarbothioate (2.0 g, 6.8 mmol) and N,N-diisopropylethylamine (4.6 mL, 27.0 mmol) in tetrahydrofuran (200 mL). The reaction mixture is allowed to warm slowly to room temperature and stirred for 1 hour. The reaction is then poured into a separatory funnel containing ethyl acetate and water. The aqueous phase is acidified to pH 3 with 1N hydrochloric acid. The organic phase is washed twice with water, then with a saturated solution of sodium bicarbonate followed by brine. Drying the organic phase over magnesium sulfate and evaporation gives a solid which is chromatographed on a 200 g column of silica with acetone/hexane (15/85). Subsequent crystallization from dichloromethane/hexane affords 0.54 g (25%) of 5-[3,5-bis(1,1-dimethylethyl)-4-hydroxyphenyl]thio]-1,3,4-oxadiazol-2(3H)-one, mp 131.5°–134.0° C.

Analysis for $C_{16}H_{22}N_2O_3S$:
Calcd: C, 59.60; H, 6.88; N, 8.69.
Found: C, 59.80; H, 6.95; N, 8.44.

EXAMPLE 7

5-[[3,5-Bis(1,1-dimethylethyl)-4-hydroxyphenyl]thio]-1,3,4-oxadiazole-2(3H)-thione Thiophosgene (0.39 mL, 5.1 mmol) is added dropwise to a −78° C. solution of S-[3,5-bis(1,1-dimethylethyl)-4-hydroxyphenyl] hydrazinecarbothioate (1.5 g, 5.1 mmol) in tetrahydrofuran (150 mL). The reaction mixture is stirred for 10 minutes then poured into a separatory funnel containing ethyl acetate and aqueous sodium bicarbonate. The organic phase is washed three times with water and once with brine. Drying the organic phase over magnesium sulfate and evaporation gives a solid which is crystallized from dichloromethane/hexane affording 1.1 g (62%) of 5-[[3,5-bis(1,1-dimethylethyl)-4-hydroxyphenyl]thio]-1,3,4-oxadiazole-2(3H)-thione, mp 129.0°–131.0° C.

Analysis for $C_{16}H_{22}N_2O_2S_2$:
Calcd: C, 56.77; H, 6.55; N, 8.28.
Found: C, 57.00; H, 6.63; N, 8.19.

EXAMPLE 8

5[[3,5-Bis(1,1-dimethylethyl)-4-hydroxyphenyl]thio]-1,3,4-thiadiazol-2(3H)-one

A 12.5% solution of phosgene in toluene (8.6 mL, 9.6 mmol) is added dropwise to a −78° C. solution of 3,5-bis(1,1-dimethylethyl)-4-hydroxyphenyl hydrazinecarbodithioate (1.5 g, 4.8 mmol) and N,N-diisopropylethylamine (3.3 mL, 19.2 mmol) in tetrahydrofuran (150 mL). The reaction mixture is stirred for 10 minutes then poured into a separatory funnel containing ethyl acetate and water. The pH of the aqueous phase is adjusted to 3 with 1N hydrochloric acid. The organic phase is washed twice with water, then with a saturated solution of sodium bicarbonate followed by brine. Drying over magnesium sulfate and evaporation of the solvents gives a solid which is crystallized twice from isopropyl ether/hexane to afford 0.7 g (43%) of 5-[[3,5-bis(1,1-dimethylethyl) -4-hydroxyphenyl]thio]-1,3,4-thiadiazol-2(3H)-one, mp 194°–197° C. (dec).

Analysis for $C_{16}H_{22}N_2O_2S_2$:
Calcd: C, 56.77; H, 6.55; N, 8.28; S, 18.95.
Found: C, 56.62; H, 6.41; N, 7.97; S, 18.57.

EXAMPLE 9

5-[[3,5-Bis(1,1-dimethylethyl)-4-hydroxyphenyl]thio]-1,3,4-thiadiazole-2(3H)-thione Thiophosgene (0.37 mL, 4.8 mmol) is added dropwise to a −78° C. solution of 3,5-bis(1,1-dimethylethyl)-4-hydroxyphenyl hydrazinecarbodithioate (1.5 g, 4.8 mmol) in tetrahydrofuran (150 mL). The reaction mixture is stirred for 10 minutes then poured into a separatory funnel containing ethyl acetate and aqueous sodium bicarbonate. The organic phase is washed three times with water and once with brine. Drying the organic phase over magnesium sulfate and evaporation gives a solid which is crystallized from ethyl acetate/hexane to afford 1.5 g (88%) of 5-[[3,5-bis(1,1-dimethylethyl)-4-hydroxyphenyl]thio]-1,3,4thiadiazole-2(3H)-thione, mp 181.0°–185.5° C.

Analysis for $C_{16}H_{22}N_2OS_3$:
Calcd C, 54.20; H, 6.25; H, 7.90.
Found: C, 53.84; H, 6.24; N, 7.72.

EXAMPLE 10

2,6-Bis(1,1-dimethylethyl)-4-[(1,3,4-thiadiazol-2-yl)thio]-phenol

A catalytic amount of p-toluenesulfonic acid (25 mg) is added to a stirring solution of 3,5-bis(1,1-dimethylethyl)-4-hydroxyphenyl hydrazinecarbodithioate (0.50 g, 1.6 mmol) and triethyl orthoformate (4 mL, 24 mmol) in ethanol (15 mL). After 10 minutes, 10 mL of 1N hydrochloric acid is added and stirring is continued for 30 minutes. The reaction mixture is diluted with ethyl acetate and washed twice with saturated solutions of sodium bicarbonate, twice with water, and once with brine. Drying the organic phase over magnesium sulfate and evaporation gives a crude product which is crystallized from dichloromethane/hexane to afford 0.37 g (72%) of 2,6-bis(1,1-dimethylethyl)-4-[1,3,4 -thiadiazol-2-yl)thio]-phenol, mp 182.5°–183.5° C.

Analysis for $C_{16}H_{22}N_2OS_2$:
Calcd: C, 59.59; H, 6.88; N, 8.69.
Found: C, 59.80; H, 6.93; N, 8.55.

EXAMPLE 11

Methyl 3-[[3,5-bis(1,1-dimethylethyl)-4-hydroxyphenyl]-thio]-propanoate (Ref. U.S. Pat. No. 4,539,159).

Methyl acrylate (1.1 g, 12.6 mmol) and triethylamine (0.5 mL, 0.4 mmol) are sequentially added to a room temperature solution of 2,6-bis(1,1-dimethylethyl)-4-mercaptophenol (3.0 g, 12.6 mmol) in acetonitrile (6 mL). The reaction is stirred for 1.5 hours and then evaporated under high vacuum to give 3.7 g (90%) of the crude product. A small portion is chromatographed on a silica column with ethyl acetate/hexane (1/9) to afford an analytically pure sample of methyl 3-[[3,5-bis(1,1-dimethylethyl)-4-hydroxyphenyl]thio]propanoate, mp 64.0°–66.0° C.

Analysis for $C_{18}H_{28}O_3S$:
Calcd: C, 66.63; H, 8.70; S, 9.88.
Found: C, 66.78; H, 8.74; S, 9.92.

EXAMPLE 12

3-[[3,5-Bis(1,1-dimethylethyl)-4-hydroxyphenyl]thio]propanoic acid hydrazide

Hydrazine monohydrate (16 mL, 324 mmol) is added to a room temperature solution of methyl 3-[[3,5-bis-(1,1-dimethylethyl)-4-hydroxyphenyl]thio]propanoate (3.5 g, 10.8 mMol) in methanol (110 mL). The reaction mixture is heated at reflux for 2 hours, then cooled, diluted with ethyl acetate and washed six times with water and once with brine. Drying the organic phase over magnesium sulfate and evaporation provides a crude solid which is chromatographed on a column of silica with methanol/chloroform (5/95) to afford 2.4 g (64%) of 3-[[3,5-bis(1,1-dimethylethyl)-4-hydroxyphenyl]thio]propanoic acid hydrazide, mp 107.0°–110.0° C.

Analysis for $C_{17}H_{28}N_2O_2S$: Calcd: C, 62.93; H, 8.70; N, 8.63; S, 9.88. Found: C, 62.66; H, 8.61; N, 8.49; S, 9.78.

EXAMPLE 13

5-[2-[[3,5-Bis(1,1-dimethylethyl)-4-hydroxyphenyl]thio]ethyl]-1,3,4-oxadiazol-2(3H)-one A 12.5% solution of phosgene in toluene (5.5 mL, 6.2 mmol) is added dropwise to a −78° C. solution of 3-[[3,5-bis(1,1-dimethylethyl)-4-hydroxyphenyl]thio]propanoic acid hydrazide (1.0 g, 2.94 mmol) in tetrahydrofuran (100 mL). The reaction mixture is stirred for 10 minutes then poured into a separatory funnel containing ethyl acetate and aqueous sodium bicarbonate. The organic phase is washed three times with water and once with brine. Drying the organic phase over magnesium sulfate and evaporation gives a heavy oil which is chromatographed on a 100 g column of silica with methanol/chloroform (3/97). After coevaporation with dichloromethane the product solidifies affording 0.64 g (63%) of 5-[2-[[3,5-bis-(1,1-dimethylethyl)-4-hydroxyphenyl]thio]ethyl]-1,3,4-oxadiazol-2(3H)-one, mp 86.0°–87.5° C.

Analysis for $C_{18}H_{26}N_2O_3S$: Calcd: C, 61.69; H, 7.48; N, 7.99; S, 9.15. Found: C, 61.51; H, 7.51; N, 7.85; S, 8.87.

EXAMPLE 14

5-[2-[3,5-Bis(1,1-dimethylethyl)-4-hydroxyphenyl]thio]ethyl-1,3,4-oxadiazole-2(3H)-thione Thiophosgene (0.34 mL, 4.40 mmol) is added dropwise to a −78° C. solution of 3-[[3,5-bis(1,1-dimethylethyl)-4-hydroxyphenyl]thio]propanoic acid hydrazide (1.5 g, 4.40 mmol) in tetrahydrofuran (150 mL). The reaction mixture is stirred for 10 minutes then poured into a separatory funnel containing ethyl acetate and aqueous sodium bicarbonate. The organic phase is washed three times with water and once with brine. Drying the organic phase over magnesium sulfate and evaporation gives a heavy oil which is crystallized from ethyl acetate/hexane to afford 1.0 g (59%) of 5-[2-[[3,5-bis(1,1-dimethylethyl)-4-hydroxyphenyl]thio]ethyl]-1,3,4-oxadiazole-2(3H)-thione, mp 123.5°–124.5° C.

Analysis for $C_{18}H_{26}N_2O_2S_2$: Calcd: C, 58.98; H, 7.15; N, 7.64; S, 17.50. Found: C, 59.08; H, 7.18; N, 7.53; S, 17.36.

EXAMPLE 5

2,6-Bis(1,1-dimethylethyl)-4-[2-(1,3,4-oxadiazol-2-yl)ethyl]thio]phenol

A catalytic amount of p-toluenesulfonic acid (25 mg) is added to a stirred solution of 3-[[3,5-bis(1,1-dimethylethyl)-4-hydroxyphenyl]thio]propanoic acid hydrazide (0.50 g, 1.54 mmol) in triethyl orthoformate (10 mL). After 30 minutes, 10 mL of 1N hydrochloric acid is added and stirring is continued for 30 minutes. The reaction mixture is diluted with ethyl acetate and washed twice with a saturated solution of sodium bicarbonate, twice with water and once with brine. Drying the organic phase over magnesium sulfate and evaporation gives a crude product which is chromatographed on a column of silica with ethyl acetate/hexane (1/9 then ½) to afford 0.33 g (64%) of 2,6-bis(1,1-dimethylethyl)-4-[[2-(1,3,4-oxadiazol-2-yl)ethyl]thio]phenol, mp 87.5°–89.0° C.

Analysis for $C_{18}H_{26}N_2O_2S$: Calcd: C, 64.64; H, 7.83; N, 8.38; S, 9.59. Found: C, 64.50; H, 7.83; N, 8.24; S, 9.55.

EXAMPLE 16

4-[2-(5-Amino-1,3,4-oxadiazol-2-yl)ethyl]thio]-2,6-bis(1,1-dimethylethyl)phenol

A solution of 3-[[3,5-bis(1,1-dimethylethyl)-4-hydroxyphenyl]thio]propanoic acid hydrazide (0.50 g, 1.54 mmol) in dioxane (15 mL) is added to a solution of sodium bicarbonate (0.14 g, 1.62 mmol) in water (4 mL). Cyanogen bromide (0.17 g, 1.62 mmol) is added in four equal portions at 1-minute intervals, and stirring is continued for 5 hours. The reaction mixture is diluted with ethyl acetate and sequentially washed with aqueous sodium bicarbonate, water, and brine. Drying the organic phase over magnesium sulfate and evaporation provides a solid which is crystallized from ethyl acetate/hexane to give 0.42 g (78%) of 4-[[2-(5-amino-1,3,4-oxadiazol-2-yl)ethyl]thio]-2,6-bis(1,1-dimethylethyl)phenol, mp 172.0°–174.0° C.

Analysis for $C_{18}H_{27}N_3O_2S$: Calcd: C, 61.86; H, 7.79; N, 12.02; S, 9.17. Found: C, 61.79; H, 7.66; N, 11.96; S, 9.10.

EXAMPLE 17

5-[2-[[3,5-Bis(1,1-dimethylethyl)-4-hydroxyphenyl]sulfinyl]ethyl]-1,3,4-oxadiazol-2(3H)-one m-Chloroperbenzoic acid (1.30 g, 6.0 mmol) is added in eight portions at 5-minute intervals to a 0° C. solution of 3-[[3,5-bis(1,1-dimethylethyl)-4-hydroxyphenyl]thio]propanoic acid hydrazide (2.25 g, 6.4 mmol) in dichloromethane (64 mL). The reaction mixture is stirred at 0° C. for 2.25 hours, then diluted with ethyl acetate and washed three times with a saturated solution of sodium bicarbonate, then with water and brine. Drying the organic phase over magnesium sulfate and evaporation gives a crude product which is chromatographed on a column of silica with ethyl acetate/hexane (3/1) to afford 1.92 g of a glassy solid.

EXAMPLE 18

5-[2-[[3,5-Bis(1,1-dimethylethyl)-4-hydroxyphenyl]-sulfonyl]ethyl]-1,3,4-oxadiazol-2(3H)-one m-Chloroperbenzoic acid (0.39 g, 1.83 mmol) is added in four portions at 5-minute intervals to a 0° C. solution of 5-[2-[[3,5-bis(1,1-dimethylethyl)-4-hydroxyphenylsulfinylethyl]-1,3,4-oxadiazol-2(3H)-one (0.50 g, 1.36 mmol) in dichloromethane (15 mL). The reaction mixture is stirred at 0° C. for an hour, then diluted with ethyl acetate and washed three times with a saturated solution of sodium bicarbonate, then with water followed by brine. Drying the organic phase over magnesium sulfate and evaporation gives a crude product which is chromatographed on a column of silica with ethyl acetate/hexane (1/1) to afford a foam which is crystallized from dichloromethane/hexane to give 0.42 g (81%) of 5-2-[[3,5-bis(1,1-dimethylethyl)-4-hydroxyphenyl]sulfonyl]ethyl]-1,3,4-oxadiazol-2(3H)-one, mp 161.5°–162.5° C.

Analysis for $C_{18}H_{26}N_2O_5S$: Calcd: C, 56.52; H, 6.85; N, 7.32; S, 8.38. Found: C, 56.24; H, 6.92; N, 7.23; S, 8.72.

EXAMPLE 19

3-[[3,5-Bis(1,1-dimethylethyl)-4-hydroxyphenyl]thio]-propanoic acid 2-formylhydrazide A solution of 3-[[3,5-bis(1,1-dimethylethyl)-4-hydroxyphenyl]thio]propanoic acid hydrazide (0.70 g, 2.16 mmol) in 96% formic acid (5.6 mL) is stirred overnight. The reaction mixture is concentrated in vacuo, diluted with ethyl acetate and washed once with a saturated solution of sodium bicarbonate, twice with water, and once with brine. Drying the organic phase over magnesium sulfate and evaporation gives an oil which is crystallized from ethyl acetate/hexane to afford 0.68 g (89%) of 3-[[3,5-bis(1,1-dimethylethyl)-4-hydroxyphenyl]thio]propanoic acid 2-formylhydrazide, mp 158.0°–159.0° C.

Analysis for $C_{18}H_{28}N_2O_3S$: Calcd: C, 61.33; H, 8.01; N, 7.95; S, 9.10. Found: C, 61.35; H, 8.22; N, 7.86; S, 9.05.

EXAMPLE 20

2,6-Bis(1,1-dimethylethyl)-4-[[2-(1,3,4-thiadiazol-2-yl)ethyl]thio]-phenol

Phosphorous pentasulfide (0.28 g, 1.28 mmol) is added to a solution of 3-[[3,5-bis(1,1-dimethylethyl)-4-hydroxyphenyl]thio]propanoic acid 2-formylhydrazide (0.45 g, 1.28 mmol) in dioxane (13 mL) and stirred overnight at 45° C. The reaction mixture is diluted with ethyl acetate and washed twice with 1N sodium hydroxide, three times with water, and twice with brine. Drying the organic phase over magnesium sulfate and evaporation gives an oil which is crystallized from methanol/water to afford 0.36 g (80%) of 2,6-bis(1,1-dimethylethyl)-4-[[2-(1,3,4-thiadiazol-2-yl)ethyl]thio]-phenol, mp 118.0°–120.0° C.

Analysis for $C_{18}H_{26}N_2OS_2$: Calcd: C, 61.67; H, 7.48; N, 7.99. Found: C, 61.35; H, 7.51; N, 7.79.

EXAMPLE 21

Methyl 3,5-bis(1,1-dimethylethyl)-4-hydroxybenzenepropanoate

Methyl 3,5-bis(1,1-dimethylethyl)-4-hydroxybenzenepropanoate is prepared according to the method of U.S. Pat. No. 4,659,863, assigned to the Ethyl Corporation, having as inventor Lester P. J. Burton.

EXAMPLE 22

3,5-Bis(1,1-dimethylethyl)-4-hydroxybenzenepropanoic acid hydrazide.

Hydrazine monohydrate (232 mL, 468 mmol) is added to a room temperature solution of methyl 3,5-bis(1,1-dimethylethyl)-4-hydroxybenzene-propanoate (11.4 g, 39 mmol) in methanol (500 mL). The reaction mixture is heated at reflux for 2 hours, cooled, diluted with ethyl acetate and washed six times with water and once with brine. Drying the organic phase over magnesium sulfate and evaporation to 100 mL yields 9.25 g of colorless crystals. Further evaporation yields 0.84 g, therefore, providing a total of 10.09 g (88%) of 3,5-bis(1,1-dimethylethyl)-4-hydroxybenzenepropanoic acid hydrazide, mp 153.0°–154.5° C.

Analysis for $C_{17}H_{28}N_2O_2$: Calcd: C, 69.83; H, 9.65; N, 9.58. Found: C, 69.80; H, 9.80; N, 9.40.

EXAMPLE 23

5-[2-[3,5-bis(1,1-dimethylethyl)-4-hydroxyphenyl]ethyl]-1,3,4-oxadiazol-2(3H)-one A 12.5% solution of phosgene in toluene (10.7 mL, 12.0 mmol) is added dropwise to a −78° C. solution of 3,5-bis(1,1-dimethylethyl)-4-hydroxybenzenepropanoic acid hydrazide in tetrahydrofuran (200 mL). The reaction mixture is stirred for 10 minutes then poured into a separatory funnel containing ethyl acetate and aqueous sodium bicarbonate. The organic phase is washed three times with water and once with brine. Drying the organic phase over magnesium sulfate and evaporation gives a crude product which is crystallized from hexane to afford 1.6 g (74%) of 5-[2-[3,5-bis(1,1-dimethylethyl)-4-hydroxyphenyl]ethyl]-1,3,4-oxadiazol-2(3H)-one, mp 120.0°–123.0° C.

Analysis for $C_{18}H_{26}N_2O_3$: Calcd: C, 67.90; H, 8.23; N, 8.80. Found: C, 67.58; H, 8.17; N, 8.68.

EXAMPLE 24

5-[2-[3,5-bis(1,1-dimethylethyl)-4-hydroxyphenyl]ethyl]-1,3,4-oxadiazole-2(3-thione Thiophosgene (0.55 mL, 6.80 mmol) is added dropwise to a −78° C. solution of 3,5-bis(1,1-dimethylethyl)-4-hydroxybenzenepropanoic acid hydrazide (2.0 g, 6.8 mmol) in tetrahydrofuran (200 mL). The reaction mixture is stirred for 10 minutes then poured into a separatory funnel containing ethyl acetate and aqueous sodium bicarbonate. The organic phase is washed three times with water and once with brine. Drying the organic phase over magnesium sulfate and evaporation gives a heavy oil which is crystallized from ethyl acetate/hexane. The product is chromatographed on a column of silica with ethyl acetate/dichloromethane (5/95) and recrystallized from dichloromethane/hexane to afford 0.36 g (16%) of 5-[2-[3,5-bis(1,1-dimethylethyl)-4-hydroxyphenyl]ethyl]-1,3,4-oxadiazole-2(3H)-thione, mp 164.5°–165.5° C.

Analysis for $C_{18}H_{26}N_2O_2S$: Calcd: C, 64.64; H, 7.83; N, 8.38. Found: C, 64.43; H, 7.69; N, 8.47.

EXAMPLE 25

2,6-Bis(1,1-dimethylethyl)-4-[2-(1,3,4-oxadiazol-2-yl)-ethyl]phenol

A catalytic amount of p-toluenesulfonic acid (25 mg) is added to a stirring solution of 3,5-bis(1,1-dimethylethyl)-4-hydroxybenzenepropanoic acid hydrazide (0.50 g, 1.71 mmol) in triethyl orthoformate (10 mL). After 30 minutes, 10 mL of 1N hydrochloric acid is added, and stirring is continued for 30 minutes. The reaction mixture is diluted with ethyl acetate and washed twice with a saturated solution of sodium bicarbonate, twice with water, and once with brine. Drying the organic phase over magnesium sulfate and evaporation gives a crude product which is chromatographed on a column of silica with ethyl acetate/hexane (1/9 then ¼) to afford 0.34 g (67%) of 2,6-bis(1,1-dimethylethyl)-4-[2-(1,3,4-oxadiazol-2-yl)ethyl]phenol, mp 100.0°–101.0° C.

Analysis for $C_{18}H_{26}N_2O_2$: Calcd: C, 71.49; H, 8.66; N, 9.26. Found: C, 71.23; H, 8.53; N, 8.89.

EXAMPLE 26

4-[2-(5-Amino-1,3,4-oxadiazol-2-yl)ethyl]-2,6-bis(1,1-dimethylethyl)phenol

A solution of 3,5-bis(1,1-dimethylethyl)-4-hydroxybenzenepropanoic acid hydrazide (0.50 g, 1.71 mmol) in dioxane (15 mL) is added to a solution of sodium bicarbonate (0.16 g, 1.88 mmol) in water (4 mL). Cyanogen bromide (0.20 g, 1.88 mmol) is then added in 4 equal portions at 1-minute intervals, and stirring is continued for 5 hours. The reaction mixture is diluted with ethyl acetate and sequentially washed with aqueous sodium bicarbonate, water, and brine. Drying the organic phase over magnesium sulfate and evaporation provides a solid which is crystallized from ethyl acetate/hexane followed by methanol/water to give 0.32 g (59%) of 4-[2-(5-amino-1,3,4-oxadiazol-2-yl)ethyl]-2,6-bis(1,1-dimethylethyl)phenol, mp 220.0°–221.0° C.

Analysis for $C_{18}H_{27}N_3O_2$: Calcd: C, 68.11; H, 8.57; 3.24. Found: C, 67.93; H, 8.43; N, 13.18.

EXAMPLE 27

3,5-Bis(1,1-dimethylethyl)-4-hydroxy-α-oxo-benzeneacetic acid, methyl ester

A dichloromethane (50 mL) solution of 13.6 g (106.5 mmol, 1.1 equiv.) of methyloxalylchloride is added over 15 minutes to a 0° C. stirred slurry of 14.2 g (106.5 mmol, 1.1 equiv.) of AlCl₃ in 100 mL of dichloromethane under nitrogen atmosphere. The reaction is stirred at 0° C. for 5 minutes and treated with a dichloromethane (50 mL) solution of 20.0 g (96.9 mmol) of 2,6-di-t-butylphenol over 30 minutes. The reaction is stirred for 3 hours and poured onto 700 mL of ice water and the layers separated. The aqueous layer is extracted with diethyl ether (3×200 mL). The combined organic layers are washed with aqueous 1N HCl (200 mL), water (4×200 mL) and saturated aqueous NaCl, dried over Na₂SO₄ and concentrated in vacuo to give a yellow solid. Recrystallizing from n-pentane gives a first crop of 8.40 g (mp 85°–86° C.) and a second crop of 4.45 g (mp 82.5°–84° C.). The total yield is 12.85 g (28.33 g theor., 45%).

Anal for $C_{17}H_{24}O_4$: Calcd: C, 69.84; H, 8.27. Found: C, 69.83; H, 8.22.

EXAMPLE 28

3,5-Bis(1,1-dimethylethyl)-4-hydroxy-α-oxo-benzeneacetic acid 3,5-Bis(1,1-dimethylethyl)-4-hydroxy-α-oxo-benzeneacetic acid, methyl ester (20.0 g, 68.4 mmol) and LiOH (3.2 g, 439.1 mmol) are combined in 125 mL of a water-methanol-tetrahydrofuran mixture (1:1:1). The reaction warms to ca 50° C. and is maintained at this temperature using a heating bath for 5 hours under nitrogen atmosphere. The reaction is poured onto ice water and extracted with diethyl ether (3×). The cold aqueous layer is acidified with aqueous 12N HCl and extracted with diethyl ether (3×). The combined ethereal layers from the second extraction are washed with saturated aqueous NaCl, dried over Na₂SO₄, and concentrated in vacuo to give an oil. Crystallizing from diethyl ether/pentane gives 14.0 g of a first crop (mp 125°–126° C.) and 2.7 g as a second crop (mp 124°–125.5° C.). The total yield is 16.7 g (19.0 g theor., 88%).

EXAMPLE 29

(5-Amino-1,3,4-thiadiazol-2-yl)[3,5-bis(1,1-dimethylethyl)-4-hydroxyphenyl]methanone Step 1. A solution of 11.5 g (90.6 mmol, 1.5 equiv.) of oxalyl chloride in 20 mL of dichloromethane is added dropwise (15 minutes) to a 0° C. solution of 16.6 g (59.6 mmol) of 3,5-bis(1,1-dimethylethyl-4-hydroxy-α-oxo-benzeneacetic acid in 100 mL of dichloromethane and 3 drops of N,N-dimethylformamide under a nitrogen atmosphere. The reaction is stirred at 0° C. to room temperature for 1 hour and concentrated in vacuo to give the acid chloride as a yellow-orange solid.

Step 2. A slurry of 5.43 g (59.6 mmol) of thiosemicarbazide in 150 mL of tetrahydrofuran at 0° C. under nitrogen atmosphere is treated over 15 minutes with a solution of half the above acid chloride (ca 29.8 mmol) in 45 mL of tetrahydrofuran. The resulting reaction mixture is stirred at 0° C. to room temperature for 2 hours and poured onto 700 mL of cold aqueous 0.5N HCl. Extraction of the aqueous reaction with ethyl acetate (3×200 mL), washing of the combined organic layers with saturated aqueous NaCl, drying over Na₂SO₄, and concentration in vacuo gives a foam. The foam is dissolved in 200 mL of t-butylmethylether and a yellow solid immediately is formed to give 6.32 g of the hydrazide product.

Step 3. A 0° C. slurry of 6.32 g (~15.0 mmol) of the above hydrazide in 75 mL of toluene is treated with 2.2 g (22.9 mmol) of methanesulfonic acid over 10 minutes. The reaction is warmed at 80° C. for 2 hours, cooled to room temperature, treated with water, and made basic (pH 8) with concentrated ammonium hydroxide. The mixture is extracted with dichloromethane (3×). The combined extracts were filtered, washed with saturated aqueous NaCl, and concentrated in vacuo to give an orange foam. Chromatography (flash, SiO₂, 230–400 mesh, 15×6.5 cm, 50% ethyl acetate-hexane) gives an orange foam. Recrystallization from acetone-hexane gives 0.45 g (9.94 g theor., 4.5%) of desired product as a pale yellow solid.

Anal for $C_{17}H_{23}N_3O_2S$: Calcd: C, 61.23; H, 6.95; N, 12.60; S, 9.62. Found: C, 61.32; H, 7.12; N, 12.52; S, 9.47.

EXAMPLE 30

[3,5-Bis(1,1-dimethylethyl]-4-hydroxyphenyl][5-methylthio)-1,3,4-thiadiazol-2-yl]methanone Step 1. The acid chloride of 3,5-bis(1,1-dimethylethyl)-4-hydroxy-α-oxobenzeneacetic acid (2.86 g, 10.27 mmol) is prepared in tetrahydrofuran as described in Step 1 of Example 29.

Step 2. The crude acid chloride is dissolved in 20 mL of tetrahydrofuran and treated dropwise with a tetrahydrofuran (10 mL) solution of 1.35 g (11.05 mmol, 1.08 equiv.) of hydrazinecarbodithioic acid, methyl ester (Audrieth, L. F., Scott, E. S., Kippur, P. S., *J. Org. Chem.* 1954, 19, 733).

The reaction is stirred for 3 hours, poured onto 200 mL of $H_2O$, and extracted with diethyl ether ($4 \times 50$ mL). The combined ethereal extracts are washed with saturated aqueous NaCl, dried over $Na_2SO_4$, and concentrated in vacuo to give a yellow foam.

Step 3. The foam is dissolved in 100 mL of toluene, treated with 0.5 g (2.63 mmol) of p-toluenesulfonic acid monohydrate, and warmed at 80° C. for 20 hours. The reaction is cooled to room temperature and concentrated in vacuo. The resulting residue is partitioned between water and ethyl acetate and the layers separated. The organic layer is washed with water and saturated aqueous NaCl, dried over $Na_2SO_4$, and concentrated in vacuo. Chromatography ($SiO_2$, 70–230 mesh, 10%, 20%, 40% ethyl acetate-hexane step gradient, $20 \times 4.5$ cm) gives 1.78 g (3.74 g theor., 48%) of the desired product as a yellow solid after recrystallization from diethyl ether-hexane; mp 161.5°–162.5° C.

Analysis for $C_{18}H_{24}N_2O_2S_2$: Calcd: C, 59.31; H, 6.64; N, 7.68. Found: C, 59.13; H, 6.62; N, 7.51.

EXAMPLE 31

[3,5-Bis(1,1-dimethylethyl)-4-hydroxphenyl][5(4H)-thioxo-1,3,4-thiadiazol-2-yl]methanone Sodium thiomethoxide (0.45 g, 6.42 mmol, 2.17 equiv.) is added to a room temperature solution of 1.08 g (2.96 mmol) of [3,5-bis(1,1-dimethylethyl)-4-hydroxyphenyl][5-(methylthio)-1,3,4-thiadiazol-2-yl]methanone in N,N-dimethylformamide (10 mL). The reaction becomes slightly warm and turns darker. The reaction is stirred at room temperature for 24 hours and warmed at 50° C. for 24 hours. The reaction is poured onto ice and aqueous 0.5N NaOH (100 mL) and extracted with t-butylmethylether ($2 \times 30$ mL). The aqueous layer is acidified with aqueous 12N HCl to give a yellow solid. Recrystallization from toluene gives 0.84 g (1.04 theor., 81%) of the desired product as a yellow solid, mp 194°–201° C.

Anal. for $C_{17}H_{22}N_2O_2S_2$: Calcd: C, 58.26; H, 6.33; N, 7.99. Found: C, 58,48; H, 6.38; N, 7.86.

EXAMPLE 32

2,6-Bis(1,1-dimethylethyl)-4-[2-[5-(methylthio)-1,3,4-thiadiazol-2-yl]ethyl]phenol Potassium hydroxide (0.22 g, 3.3 mM) is added to a 0° C. solution of 3,5-bis(1,1-dimethylethyl)-4-hydroxybenzenepropanoic acid hydrazide (1.0 g, 3.4 mM) and carbon disulfide (0.22 mL, 7.2 mM) in methanol (36 mL). The reaction mixture is stirred at 0° C. for 2 hours then at room temperature for 4 hours. Iodomethane (0.21 mL, 3.4 mM) is added and stirring is continued overnight. The reaction is diluted with ether and washed twice with water, once with a saturated solution of sodium bicarbonate, and once with brine. Drying the organic phase over magnesium sulfate and evaporation gives 1.2 g of crude intermediate which is dissolved in toluene (20 mL). p-Toluenesulfonic acid (0.72 g, 3.8 mM) is added to the solution and the reaction is heated at reflux for 1.5 hours. The reaction solution is cooled and filtered. The filtrate is diluted with ether and washed twice with water, once with a saturated solution of sodium bicarbonate, and once with brine. Drying the organic phase over magnesium sulfate and evaporation gives a crude product which is chromatographed on silica gel eluting with 1:9 then 2:8 ethyl acetate:hexane yielding 0.29 g (25%) of a white solid which is 2,6-bis(1,1-dimethylethyl)-4-[2-[5-(methylthio)-1,3,4-thiadiazol-2-yl]ethyl]phenol; mp 135°–139° C.

EXAMPLE 33

5-[2-3,5-Bis(1,1-dimethylethyl)-4-hydroxyphenyl]ethyl]-1,3,4-thiadiazole-2(3H)-thione Sodium thiomethoxide (0.10 g, 1.35 mM) is added to a solution of 2,6-bis(1,1-dimethylethyl)-4-[2-[5-(methythio)-1,3,4-thiadiazol-2-yl]ethyl]phenol (0.10 g, 0.27 mM) in dimethylformamide (2.7 mL). The reaction solution is heated at 80° C. for 4 hours then cooled, diluted with ethyl acetate and washed once with 1N hydrochloric acid, three times with water, and once with brine. Drying the organic phase over magnesium sulfate and evaporation gives 0.10 g of a white solid which is recrystallized from ethyl acetate/hexane yielding 0.08 g (84%) of colorless crystals which is 5-[2-[3,5bis(1,1-dimethylethyl)-4-hydroxyphenyl]ethyl]-1,3,4-thiadiazole-2(3H)-thione; mp 213.0°–214.0° C.

Analysis for $C_{18}H_{26}N_2OS_2$: Calcd: C, 61.67; H, 7.48; N, 7.99. Found: C, 61.77; H, 7.40; N, 8.03.

EXAMPLE 34

5-[2-[3,5-Bis(1,1-dimethylethyl)-4-hydroxyphenyl]ethyl]-1,3,4-thiadiazol-2(3H)-one Two equal portions of 80% m-chloroperbenzoic acid (0.10 g, 0.48 mM) are added to a 0° C. solution of 2,6-bis(1,1-dimethylethyl)-4-[2-[5-(methylthio)-1,3,4-thiadiazol-2-yl]ethyl]phenol (0.86 g, 0.24 mM) in methylene chloride (4 mL) at 30 minute intervals. The reaction is allowed to warm slowly to room temperature and another portion of 80% m-chloroperbenzoic acid (0.05 g, 0.24 mM) is added. The reaction solution is stirred for 5 hours then diluted with ethyl acetate and washed five times with a saturated solution of sodium bicarbonate, once with water, and once with brine. Drying the organic phase over magnesium sulfate and evaporation gives 0.13 g of a brown oil which is dissolved in dioxane (2 mL). An aqueous solution of 50% sodium hydroxide (0.16 g, 2.0 mM) diluted with water (0.7 mL) is added and stirring is continued for 6 hours at room temperature. The dark red reaction solution is diluted with ethyl acetate and washed once with 1N hydrochloric acid, twice with water, and once with brine. Drying the organic phase over magnesium sulfate and evaporation gives a brown solid which is chromatographed on silica gel eluting with 2:8 ethyl acetate:hexane followed by crystallization from ethyl acetate/hexane yielding 0.03 g (37) of pale yellow crystals which are 5-[2-[3,5-bis(1,1-dimethylethyl)-4-hydroxyphenyl]ethyl]-1,3,4-thiadiazol-2(3H)-one; mp 149.5°–151.0° C.

Analysis for $C_{18}H_{26}N_2O_2S$: Calcd: C, 64.64; H, 7.84; N, 8.38. Found: C, 64.54; H, 7.79; N, 8.00.

EXAMPLE 35

2,6-Bis(1,1-dimethylethyl)-4-[[5-(methylthio)-1,3,4-thiadiazol-2-yl]thio]phenol

A solution of 4-bromo-2,6-di-t-butylphenol (3.0 g, 10.5 mmol), 5-methylthio-1,3,4-thiadiazole-2-thiol (2.0 g, 12.2 mmol), and 1,8-diazabicyclo-[5.4.0]undecen-7-ene (1.8 mL, 12.0 mmol) in dimethylformamide (120 mL) is stirred at 55° to 70° C. for 48 hours. The reaction mixture is cooled and diluted with ether then washed four times with water and once with brine. Drying the organic phase over magnesium sulfate and evaporation gives a solid residue which is crystallized from ethyl acetate/hexane yielding 2.4 g (63%) of analytically pure light brown platelets; mp 144.0°–145.0° C. The mother liquor is chromatographed on silica gel eluting with 1:9 then 2:8 ethyl acetate:hexane to yield an additional 0.7 g (18%) of 2,6-bis(1,1-dimethylethyl)-4-[[5-(methylthio)-1,3,4-thiadiazol-2-yl]thio]phenol.

Analysis for $C_{17}H_{24}N_2OS_3$: Calcd: C, 55.40; H, 6.56; N, 7.60; S, 26.10. Found: C, 55.64; H, 6.47; N, 7.56; S, 25.80.

EXAMPLE 36

2,6-Bis(1,1-dimethylethyl)-4-5-(methylsulfinyl)-1,3,4-thiadiazol-2-yl]thio]phenol A solution of 2,6-bis(1,1-dimethylethyl)-4-[[5-(methylthio)-1,3,4-thiadiazol-2-yl]thio]phenol (0.25 g, 0.68 mmol) and sodium perborate (0.11 g, 0.71 mmol) in acetic acid (20 mL) is stirred at room temperature for 7 hours then stored at 0° C. overnight. The reaction mixture is diluted with ether and washed three times with water, then with a saturated solution of sodium bicarbonate and once with brine. Drying the organic phase over magnesium sulfate and evaporation gives a white solid which is chromatographed on silica gel eluting with a gradient of ethyl acetate:hexane (1:9, 2:8, 3:7, then 1:1) yielding 0.16 g (61%) of 2,6-bis(1,1-dimethylethyl)-4-[[5-(methylsulfinyl)-1,3,4-thiadiazol-2-yl]thio]phenol; mp 162.0°–163.5° C.

Analysis for $C_{17}H_{24}N_2O_2S_3$: Calcd: C, 53.09; H, 6.29; N, 7.28. Found: C, 53.47; H, 6.23; N, 7.36.

EXAMPLE 37

[5-[[3,5-Bis(1,1-dimethylethyl)-4-hydroxyphenyl]thio]-1,3,4-thiadiazol-2-yl]cyanamide Cyanamide (0.11 g, 2.60 mmol) is added to a suspension of potassium t-butoxide (0.26 g, 2.27 mmol) in t-butanol (6.5 mL) and stirred at room temperature for 30 minutes. 2,6-Bis(1,1-dimethylethyl)-4-[[5-(methylsulfinyl)-1,3,4-thiadiazol-2-yl]thio]phenol (0.25 g, 0.65 mmol) is added and stirring is continued at 55° C. for 2 hours. The reaction mixture is diluted with ethyl acetate and washed with dilute aqueous hydrochloric acid, then three times with water and once with brine. Drying the organic phase over magnesium sulfate and evaporation gives an oil which is dissolved in acetonitrile and concentrated slowly in vacuo yielding 0.15 g (64%) of yellow crystals which are [5-[[3,5-bis(1,1-dimethylethyl)-4-hydroxyphenyl]thio]-1,3,4-thiadiazol-2-yl]cyanamide.

Analysis for $C_{17}H_2N_4OS_2$: Calcd: C, 56.33; H, 6.12; N, 15.45; S, 17.69. Found: C, 56.16; H, 6.12; N, 15.55; S, 18.04.

EXAMPLE 38

N-[5-[[3,5-Bis(1,1-dimethylethyl)-4-hydroxyphenyl]thio]-1,3,4-thiadiazol-2-yl]guanidine Guanidine hydrochloride (0.24 g, 2.60 mmol) is added to a suspension of potassium t-butoxide (0.26 g, 2.27 mmol) in t-butanol (6.5 mL) and stirred at room temperature for 30 minutes. 2,6-Bis(1,1-dimethylethyl)-4-[[5-(methylsulfinyl)-1,3,4-thiadiazol-2-yl]thio]phenol (0.25 g, 0.65 mmol) is added and stirring is continued at 55° C. for 4 hours then at 70° C. for 2.5 hours. The reaction mixture is diluted with ethyl acetate and water. The aqueous phase is neutralized with 1N hydrochloric acid and discarded. The organic phase is washed three times with water and once with brine. Drying the organic phase over magnesium sulfate and evaporation gives a light brown oil which is dissolved in acetonitrile and evaporated to a semi-solid. The material is suspended in ether and filtered to give 0.10 g (39%) of light brown crystals which are N-[5-[[3,5-bis(1,1-dimethylethyl)-4-hydroxyphenyl]thio]-1,3,4-thiadiazol-2-yl]guanidine; mp 248.0°–249.0° C.

Analysis for $C_{17}H_{25}N_5OS_2$: Calcd: C, 53.80; H, 6.64; N, 18.45. Found: C, 53.69; H, 6.60; N, 18.82.

EXAMPLE 39

2,6-Di-t-butyl-1,4-dihydroquinone

Prepared according to the method of Matti Karhu; J. Chem. Soc., Perkin Trans. I; 303, 1981.

EXAMPLE 40

3,5-Bis(1,1-dimethylethyl)-4-hydroxyphenyl carbonothioic acid hydrazide

A solution of 2,6-di-butyl-1,4-dihydroquinone (2.0 g, 9.0 mmol) and N,N-diisopropylethylamine (2.3 mL, 13.5 mmol) in toluene (50 mL) is added to a 0° C. solution of thiophosgene (1.0 mL, 13.5 mmol) in toluene (40 mL). The reaction mixture is stirred for 30 minutes at 0° C. and hydrazine monohydrate (4.4 mL, 90.0 mmol) is added. The ice bath is removed and the reaction is stirred for 2 hours. The reaction mixture is diluted with ether and washed four times with water and once with brine. Drying the organic phase over magnesium sulfate and evaporation gives a brown oil which is chromatographed on silica gel eluting with 2:8 then 4:6 ethyl acetate:hexane yielding 1.9 g (72%) of a light brown solid. An analytical sample is obtained by crystallization from ether/hexane to give light brown crystals of 3,5-bis(1,1-dimethylethyl)-4-hydroxyphenyl carbonothioic acid hydrazide; mp 102°–106° C.

Analysis for $C_{15}H_{24}N_2O_2S$: Calcd: C, 60.78; H, 8.16; N, 9.45; S, 10.82. Found: C, 60.80: H, 7.97: N, 9.30: S, 10.70

EXAMPLE 41

5-[3,5-Bis(1,1-dimethylethyl)-4-hydroxyphenoxy]-1,3,4-thiadiazol-2(3H)-one

A 12.5% solution of phosgene in toluene (1.27 mL, 1.42 mmol) is added dropwise to a −78° C. solution of 3,5-bis(1,1-dimethylethyl)-4-hydroxyphenyl carbonothioic acid hydrazide (0.20 g, 0.67 mmol) in tetrahydrofuran (15 mL). The reaction mixture is stirred for 30 minutes, diluted with ethyl acetate, and washed three times with water and once with brine. Drying the organic phase over magnesium sulfate and coevaporation with ether/hexane gives a solid which is crystallized from ether/hexane to give 0.14 g (62%) of pale yellow crystals which are 5-[3,5-bis(1,1-dimethylethyl)-4-hydroxyphenoxy]-1,3,4-thiadiazol-2(3H)-one; mp 184.5°–188.0° C.

Analysis for $C_{16}H_{22}N_2O_3S$: Calcd: C, 59.60; H, 6.88; N, 8.69; S, 9.94. Found: C, 59.22; H, 6.55; N, 8.56; S, 9.87.

EXAMPLE 42

5-[3,5-Bis(1,1-dimethylethyl)-4-hydroxyphenoxy]-1,3,4-thiadiazol-2(3H)-thione

Thiophosgene (57 μL, 0.74 mmol) is added dropwise to a −78° C. solution of 3,5-bis(1,1-dimethylethyl)-4-hydroxyphenyl carbonothioic acid hydrazide (0.20 g, 0.67 mmol) in tetrahydrofuran (15 mL). The reaction mixture is stirred for 30 minutes, diluted with ethyl acetate, and washed three times with water and once with brine. Drying the organic phase over magnesium sulfate and coevaporation with ether/hexane gives a solid which is crystallized from methylene chloride/hexane to give 0.18 g (80%) of a pale yellow powder which is 5-[3,5-bis(1,1-dimethylethyl)-4-hydroxyphenoxy]-1,3,4-thiadiazol-2(3H)-thione; mp 181°–186° C.

Analysis: $C_{16}H_{22}N_2O_2S_2$: Calcd: C, 56.77; H, 6.55; N, 8.28; S, 18.95. Found: C, 56.91; H, 6.56; N, 7.98; S, 19.07.

EXAMPLE 43

2,6-Bis(1,1-dimethylethyl)-4-[[5-(methylthio)-1,3,4-thiadiazol-2-yl]oxy]phenol

A solution of 1N sodium hydroxide (2.95 mL, 2.95 mmol) is added dropwise to a solution of 5-[3,5-bis(1,1-dimethylethyl)-4-hydroxyphenoxy]-1,3,4-thiadiazole-2(3H)-thione (1.00 g, 2.95 mmol) and iodomethane (0.74 mL, 11.8 mmol) in methanol (30 mL). The reaction solution is diluted with ether and washed once with dilute aqueous hydrochloric acid, three times with water, and once with brine. Drying the organic phase over magnesium sulfate and evaporation followed by crystallization from hexane gives 0.83 g (80%) of tan crystals which are 2,6-bis(1,1-dimethylethyl)-4-[[5-(methylthio)-1,3,4-thiadiazol-2-yl]oxy]phenol; mp 132.0°–134.0° C.

Analysis for $C_{17}H_{24}N_2O_2S_2$: Calcd: C, 57.92; H, 6.86; N, 7.95. Found: C, 58.01; H, 6.47; N, 8.03.

EXAMPLE 44

2,6-Bis(1,1-dimethylethyl)-4-[[5-(methylsulfonyl)-1,3,4-thiadiazol-2-yl]oxy]phenol Three equal portions of 80% m-chloroperbenzoic acid (1.3 g, 6.0 mmol) are added to a −10° C. solution of 2,6-bis(1,1-dimethylethyl)-4-[[5-(methylthio)-1,3,4-thiadiazol-2-yl]oxy]phenol (0.70 g, 2.0 mmol) in methylene chloride (20 mL) at 30-minute intervals. Stirring is continued for 1 hour at −10° C. then at room temperature for 2 hours. The reaction solution is diluted with ether and washed three times with a saturated solution of sodium bicarbonate, once with water, and once with brine. Drying over magnesium sulfate and evaporation followed by crystallization from ether/hexane yields 0.72 g (94%) of pale yellow crystals which are 2,6-bis(1,1-dimethylethyl)-4-[[5-(methylsulfonyl)-1,3,4-thiadiazol-2-yl]oxy]phenol; mp 174.5°–175.5° C.

Analysis for $C_{17}H_{24}N_2O_4S_2$: Calcd: C, 53.10; H, 6.29; N, 7.29. Found: C, 53.00; H, 6.26; N, 7.31.

EXAMPLE 45

Ethyl [3,5-bis(1,1-dimethylethyl)-4-hydroxyphenoxy]acetate

A mixture of 2,6-di-t-butyl-1,4-dihydroquinone (5.0 g, 22.5 mmol), ethyl bromoacetate (5.0 mL, 45.0 mmol), and powdered potassium carbonate (9.3 g, 67.5 mmol) in freshly distilled tetrahydrofuran (100 mL) is stirred vigorously at a gentle reflux for 26 hours. The reaction mixture is poured into water and acidified with 6N hydrochloric acid. The aqueous phase is extracted twice with ether. The combined organic phase is washed twice with water and once with brine. Drying the organic phase over magnesium sulfate and evaporation gives an oil which is chromatographed on silica gel eluting with 2:98 then 5:95 ethyl acetate:hexane. The resulting heavy oil crystallizes to give 5.2 g (75%) of ethyl [3,5-bis(1,1-dimethylethyl)-4-hydroxyphenoxy]acetate. An analytically pure sample is obtained by recrystallization from ethanol/water; mp 54.5°–56.0° C.

Analysis for $C_{18}H_{28}O_4$: Calcd: C, 70.10; H, 9.15. Found C, 69.99; H, 9.07.

EXAMPLE 46

[3,5-Bis(1,1-dimethylethyl)-4-hydroxyphenoxy]acetic acid hydrazide

A solution of ethyl [3,5-bis(1,1-dimethylethyl)-4-hydroxyphenoxy]acetate (2.5 g, 8.1 mmol) and hydrazine monohydrate (1.2 mL, 24.3 mmol) in ethanol (40 mL) is heated at 65°–75° C. for 8 hours. The reaction mixture is cooled and poured into 500 mL of water. The solids are filtered and washed twice with water. The white solid is dried overnight at 50° C. in vacuo to give 2.1 g (87%) of [3,5-bis(1,1-dimethylethyl)-4-hydroxyphenoxy]-acetic acid hydrazide; mp 141.0°–142.5° C.

Analysis for $C_{16}H_{26}N_2O_3$: Calcd: C, 65.28; H, 8.90; N, 9.52. Found: C, 65.62; H, 8.99; N, 9.23.

EXAMPLE 47

4-(5-Amino-1,3,4-oxadiazol-2-yl)methoxy]-2,6-bis-(1,1-dimethylethyl)phenol

A solution of [3,5-bis(1,1-dimethylethyl)-4-hydroxyphenoxy]-acetic acid hydrazide (0.15 g, 0.52 mmol) in dioxane (5 mL) is added to a solution of sodium carbonate (0.04 g, 0.52 mmol) in water (1.2 mL). After stirring 10 minutes, cyanogen bromide (0.06 g, 0.52 mmol) is added and stirring is continued for 4 hours. The reaction solution is diluted with ethyl acetate and washed twice with water and once with brine. Drying the organic phase over magnesium sulfate and evaporation gives a crude residue which is chromatographed on silica gel eluting with 3:7 ethyl acetate:methylene chloride yielding 0.14 g (84%) of 4-[(5-amino-1,3,4-oxadiazol-2-yl)methoxy]-2,6-bis(1,1-dimethylethyl)-phenol; mp 177.5°–180.0° C.

Analysis for $C_{17}H_{25}N_3O_3$: Calcd: C, 63.93; H, 7.89; N, 13.15. Found: C, 63.71; H, 7.81; N, 13.18.

EXAMPLE 48

5-[[3,5-Bis(1,1-dimethylethyl)-4-hydroxyphenoxy]-methyl]-1,3,4-oxadiazol-2(3H)-one A 12.5% solution of phosgene in toluene (2.4 mL, 2.7 mmol) is added dropwise to a −78° C. of [3,5-bis(1,1-dimethylethyl)-4-hydroxyphenoxy]-acetic acid hydrazide (0.40 g, 1.36 mmol) in tetrahydrofuran (25 mL). The reaction mixture is stirred for 30 minutes, diluted with ethyl acetate, and washed three times with water and once with brine. Drying the organic phase over magnesium sulfate and evaporation gives a pale yellow oil which is crystallized from ethyl acetate/hexane yielding 0.34 g (79%) of 5-[3,5-bis(1,1-dimethylethyl)-4-hydroxyphenoxy]methyl-1,3,4-oxadiazol-2(3H)-one; mp 138.0°-140.0° C.

Analysis for $C_{17}H_{24}N_2O_4$: Calcd: C, 63.73; H, 7.55; N, 8.74. Found: C, 63.99; H, 7.49; N, 8.62.

EXAMPLE 49

5-[[3,5-Bis(1,1-dimethylethyl)-4-hydroxyphenoxy]-methyl]-1,3,4-oxadiazole-2(3H)-thione Thiophosgene (0.10 mL, 1.36 mmol) is added dropwise to a −78° C. solution of [3,5-bis(1,1-dimethylethyl)-4-hydroxyphenoxy-acetic acid hydrazide (0.40 g, 1.36 mmol) in tetrahydrofuran (25 mL). The reaction mixture is stirred for 30 minutes, diluted with ethyl acetate, and washed three times with water and once with brine. Drying the organic phase over magnesium sulfate and evaporation gives a pale yellow oil which is crystallized from ethyl acetate/hexane yielding 0.36 g (78%) of 5-[[3,5-bis(1,1-dimethylethyl)-4-hydroxyphenoxymethyl]-1,3,4-oxadiazole-2(3H)-thione, mp 195.0°-196.5° C.

Analysis for $C_{17}H_{24}N_2O_3S$: Calcd: C, 60.68; H, 7.19; N, 8.32; S, 9.53. Found: C, 60.86; H, 7.05; N, 7.96; S, 9.14.

EXAMPLE 50

[3,5-Bis(1,1-dimethylethyl)-4-hydroxyphenoxy]acetonitrile

A mixture of 2,6-di-t-butyl-1,4-dihydroquinone (3.5 g, 15.6 mmol), bromoacetonitrile (5.4 mL, 77.8 mmol), and powdered potassium carbonate (6.4 g, 46.7 mmol) in freshly distilled tetrahydrofuran (70 mL) is stirred vigorously at a gentle reflux for 72 hours. An additional amount of bromoacetonitrile (4.0 mL, 57.6 mM) is added and stirring is continued at reflux for 24 hours. The reaction mixture is cooled and diluted with ether and ethyl acetate and filtered. The filtrate is washed three times with water, once with 1N hydrochloric acid, twice with dilute aqueous sodium hydroxide, twice with water, and once with brine. Drying the organic phase with magnesium sulfate and evaporation gives an oil which is chromatographed on silica gel yielding 2.0 g (50%) of a pale yellow oil which is [3,5-bis(1,1-dimethylethyl)-4-hydroxyphenoxy] acetonitrile. A small portion is purified by Kugelrohr distillation.

Analysis for $C_{16}H_{23}NO_2$: Calcd: C, 73.53; H, 8.87; N, 5.36. Found: C, 73.66; H, 8.94; N, 5.17.

EXAMPLE 51

2-[3,5-Bis(1,1-dimethylethyl)-4-hydroxyphenoxy]ethanethioamide

Hydrogen sulfide gas is bubbled for 30 minutes into a solution of [3,5-bis(1,1-dimethylethyl)-4-hydroxyphenoxy] acetonitrile (1.16 g, 4.44 mmol) and triethylamine (0.68 mL, 4.88 mmol) in pyridine (4.5 mL). The reaction mixture is diluted with ether and washed once with dilute aqueous hydrochloric acid, three times with water, and once with brine. The organic phase is dried over magnesium sulfate and filtered. Argon is bubbled through the organic solution to remove residual hydrogen sulfide. The organic phase is concentrated in vacuo and the solid residue is crystallized from ether/hexane yielding 1.1 g (82%) of white crystals of 2-[3,5-bis((1,1-dimethylethyl)-4-hydroxyphenoxy]-ethanethioamide; mp 163.0°-164.0° C.

Analysis for $C_{16}H_{25}NO_2S$: Calcd: C, 65.05; H, 8.53; N, 4.74; S, 10.85. Found: C, 64.95; H, 8.18; N, 4.77; S, 11.08.

EXAMPLE 52

5-[[3,5-Bis(1,1-dimethylethyl)-4-hydroxyphenoxy]methyl]-1,3,4-thiadiazole-2(3H)-thione Hydrazine monohydrate (0.18 mL, 3.72 mmol) is added to a solution of 2-[3,5-bis(1,1-dimethylethyl)-4-hydroxyphenoxy]-ethanethioamide (1.10 g, 3.72 mmol) in methanol (37 mL). After stirring for 1 hour an additional amount of hydrazine monohydrate (0.18 mL, 3.73 mmol) is added and stirring is continued for 1 hour. The reaction mixture is diluted with ether and washed four times with water and once with brine. Drying the organic phase over magnesium sulfate and evaporation gives 1.16 g of a pale yellow foam which is dissolved in methanol (40 mL). To this solution is added carbon disulfide (2.4 mL, 39.7 mmol) and stirring is continued overnight. The reaction solution is diluted with ether and washed three times with water and once with brine. Drying the organic phase over magnesium sulfate and evaporation gives a solid which is crystallized from ether/hexane, followed by methanol/water, and then chromatographed on silica gel eluting with 2:3:15 acetone:methylene chloride:hexane yielding 0.14 g (10%) of a white powder which is 5-[[3,5-bis(1,1-dimethylethyl)-4-hydroxyphenoxy]methyl]-1,3,4-thiadiazole-2(3H)-thione; mp 192°-195° C.

Analysis for $C_{17}H_{24}N_2O_2S_2$: Calcd: C, 57.92; H, 6.86; N, 7.95. Found: C, 58.12; H, 6.95; N, 7.82.

EXAMPLE 53

2,6-Bis(1,1-dimethylethyl)-4-[(5-methylthio-1,3,4-thiadiazol-2-yl)methoxy]phenol A solution of 1N sodium hydroxide (1.05 mL, 1.05 mmol) is added over 5 minutes to a solution of 5-[[3,5-bis(1,1-dimethylethyl)-4-hydroxyphenoxy]-methyl]-1,3,4-thiadiazole-2(3H)-thione (0.37 g, 1.05 mmol) and iodomethane (0.26 mL, 4.20 mmol) in methanol (10 mL). The reaction is stirred for 30 minutes, then the pink precipitate is filtered and washed with methanol/water. A second crop is collected, and the combined precipitate is (71%) of pink platelets which are 2,6-bis(1,1-dimethylethyl)-4-[(5-methylthio-1,3,4-thiadiazol-2-yl)methoxy]phenol; mp 128.0°-129.5° C.

Analysis for $C_{18}H_{26}N_2O_2S_2$: Calcd: C, 58.98; H, 7.15; N, 7.64. Found: C, 59.08; H, 7.48; N, 7.65.

EXAMPLE 54

5-(Methylsulfonyl)-1,3,4-thiadiazole-2-carboxylic acid, 3,5-bis(1,1-dimethylethyl)-4-hydroxylphenyl ester and [3,5-bis(1,1-dimethylethyl)-4-hydroxyphenyl][5-(methylsulfonyl)-1,3,4-thiadiazole-2-yl]-methanone.

A 0° C. solution of 10.0 g (27.4 mmol) of [3,5-bis(1,1-dimethylethyl)-4-hydroxyphenyl]-[5-methylthio)-1,3,4-thiadiazol-2-yl]methanone in 160 mL of $CH_2Cl_2$ under $N_2$ atmosphere is treated with 18.0 g (83–89 mmol) of 80°–85° m-chloroperbenzoic acid in small portions over 30 minutes. The reaction is slowly allowed to warm to 25° C. The reaction is stirred for a total of 23 hours and partitioned between t-butylmethylether and aqueous 5% M $NaHCO_3$. The layers are separated and the organic layer is washed with aqueous 5% M $NaHCO_3$ (3×) and saturated aqueous NaCl (1×), dried over Na₂SO₄ and concentrated in vacuo to give a yellow solid. Recrystallization from t-butylmethylether/hexane gave 1.82 g (16%) of analytically pure 5-(methylsulfonyl)-1,3,4-thiadiazole-2-carboxylic acid, 3,5-bis(1,1-methylethyl)-4-hydroxyphenyl ester as a yellow solid; mp 164.5°-165.5° C. A second crop of 4.5 g (41%) of analytically pure 3,5-bis(1,1-dimethylethyl)-4-hydroxyphenyl][5-(methylsulfonyl)-1,3,4-thiadiazol-2-yl]methanone is isolated as a dark yellow solid; mp 197°-199° C.

EXAMPLE 55

N-[5-[3,5-Bis(1,1-dimethylethyl)-4-hydroxybenzoyl-1,3,4-thiadiazol-2-yl]guanidine A slurry of 0.47 g (4.92 mmol) of guanidine hydrochloride in t-BuOH under N₂ atmosphere is treated with 4.5 mL (4.5 mmol) of a 1.0M KOtBu/t-BuOH solution. The resulting mixture is treated with 1.00 g (2.52 mmol) of [3,5-bis(1,1-dimethylethyl)-4-hydroxyphenyl][5-methylsulfonyl)-1,3,4-thiadiazol-2-yl]methanone and warmed at 90° C. for 2 hours, The reaction is poured onto 75 mL of H₂O and 50 mL of ethyl acetate. The layers are separated and the aqueous layer is extracted with ethyl acetate (2×40 mL). The combined organic layers are washed with saturated aqueous NaCl, dried over Na₂SO₄, and concentrated in vacuo. Chromatography (SiO₂, 70–230 mesh, ethyl acetate eluant, 3.5×18 cm) gives a solid. Recrystallization from methanol-water gives 0.37 g (mp 267°–269° C.) of analytically pure material as a first crop and 0.13 g (mp 262°–264° C.) of a second crop also analytically pure which is N-[5-[3,5-bis(1,1-dimethylethyl)-4-hydroxybenzoyl]-1,3,4-thiadiazol-2-yl]guanidine.

We claim:
1. A compound of the formula (I)

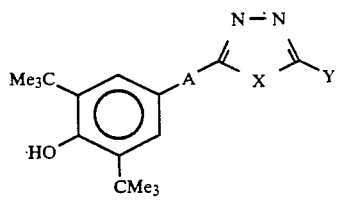

wherein
A is CO, C=NOH, S, S(O)$_n$(CH$_2$)$_m$, (CH$_2$)$_m$, S(O)$_n$, CO(CH$_2$)$_m$, O, or O(CH$_2$)$_m$;
X is O;
Y is H, OH, SH, NH$_2$, —NHC≡N,

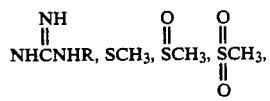

wherein
R is H or lower alkyl;
n is an integer of zero, one or two; and
m is an integer of one or two with the proviso that when A is (CH$_2$)$_m$, then Y cannot be OH.
2. A compound of claim 1 wherein A is CO.
3. A compound of claim 1 wherein A is O or S.
4. A compound of claim 1 wherein A is S(O)$_n$(CH$_2$)$_m$.
5. A compound of claim 1 wherein A is (CH$_2$)$_m$.
6. A compound of claim 1 wherein A is CO(CH$_2$)$_m$.
7. A compound of claim 1 wherein X is O.
8. A compound of claim 4 which is 2,6(1,1-dimethylethyl)-4-[[2-(1,3,4-oxadiazol-2-yl)ethyl]thio]phenol.
9. A compound of claim 4 which is 4-[[2-(5-amino-1,3,4-oxadiazol-2-yl)ethyl]thio]-2,6-bis(1,1-dimethylethyl)phenol.
10. A compound of claim 4 which is 5-[2-[3,5-bis(1,1-dimethylethyl)-4-hydroxyphenylsulfonyl]ethyl]-1,3,4-oxadiazol-2(3H)-one.
11. A compound of claim 5 which is 2,6-bis(1,1-dimethylethyl)-4-[2-(1,3,4-oxadiazol-2-yl)ethyl]phenol.
12. A compound of claim 5 which is 4-2-(5-amino-1,3,4-oxadiazol-2-yl)ethyl]-2,6-bis(1,1-dimethylethyl)-phenol.
13. A compound of claim 3 which is 5-[[3,5-bis(1,1-dimethylethyl)-4-hydroxyphenyl]thio]-1,3,4-oxadiazol-2(3H)-one.
14. A compound of claim 3 which is 5-[[3,5-bis(1,1-dimethylethyl)-4-hydroxyphenyl]thio]-1,3,4-oxadiazole-2(3H)-thione.
15. A compound of claim 4 which is 5-[2-[[3,5-bis(1,1-dimethylethyl)-4-hydroxyphenyl]thio]ethyl-1,3,4-oxadiazole-2(3H)-thione.
16. A compound of claim 4 which is 5-[2-[[3,5-bis(1,1-dimethylethyl)-4-hydroxyphenyl]sulfinyl]ethyl]-1,3,4-oxadiazol-2(3H)-one.
17. A compound of claim 4 which is 5-[2-[[3,5-bis(1,1-dimethylethyl)-4-hydroxyphenyl]sulfinyl]ethyl]-1,3,4-oxadiazol-2(3H)-one.
18. A compound of claim 1 which is 4-[(5-amino-1,3,4-oxadiazo-2-yl)methoxy]-2,6-bis-(1,1-dimethylethyl)phenol.
19. A compound of claim 1 which is 5-[[3,5-bis(1,1-dimethylethyl)-4-hydroxyphenoxy]methyl]-1,3,4-oxadiazol-2(3)-one.
20. A compound of claim 1 which is 5-[[3,5-bis(1,1-dimethylethyl)-4-hydroxyphenoxy]methyl]-1,3,4-oxadiazole-2(3H)-thione.
21. A pharmaceutical composition for use as an inhibitor of 5-lipoxygenase, cyclooxygenase or both comprising an amount which inhibits a 5-lipoxygenase, cyclooxygenase or both of a compound of the formula (I)

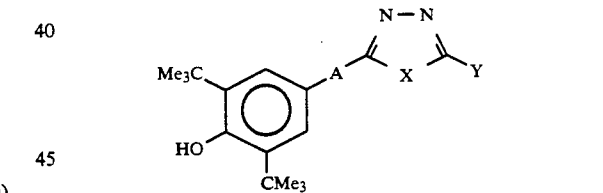

wherein
A is CO, C=NOH, S, S(O)$_n$(CH$_2$)$_m$, (CH$_2$)$_m$, S(O)$_n$, CO(CH$_2$)$_m$, O, or O(CH$_2$)$_m$;
X is O;
Y is H, OH, SH, NH$_2$, —NHC≡N,

wherein
R is H or lower alkyl;
and a pharmaceutically acceptable carrier.
22. A composition of claim 21 wherein the compound is 5-[2-[3,5-bis(1,1-dimethylethyl)-4-hydroxyphenyl]ethyl]-1,3,4-oxadiazol-2(3H)-one.
23. A method for treating an inflammatory disease or condition in a human suffering therefrom which comprises administering a composition of claim 21 in unit dosage form.

* * * * *